(12) United States Patent
Reznicek et al.

(10) Patent No.: US 10,900,952 B2
(45) Date of Patent: Jan. 26, 2021

(54) DUAL SURFACE CHARGE SENSING BIOSENSOR

(71) Applicant: International Business Machines Corporation, Armonk, NY (US)

(72) Inventors: Alexander Reznicek, Troy, NY (US); Jeng-Bang Yau, Yorktown Heights, NY (US); Bahman Hekmatshoartabari, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 0 days.

(21) Appl. No.: 16/594,885

(22) Filed: Oct. 7, 2019

(65) Prior Publication Data

US 2020/0363393 A1 Nov. 19, 2020

Related U.S. Application Data

(60) Provisional application No. 62/849,033, filed on May 16, 2019.

(51) Int. Cl.
*G01N 33/487* (2006.01)
*H01L 29/732* (2006.01)
(Continued)

(52) U.S. Cl.
CPC ... *G01N 33/48707* (2013.01); *H01L 29/0804* (2013.01); *H01L 29/0821* (2013.01);
(Continued)

(58) Field of Classification Search
CPC .................................................. G01T 1/026
See application file for complete search history.

(56) References Cited

U.S. PATENT DOCUMENTS

| 7,692,219 B1 * | 4/2010 | Holm-Kennedy ..... B82Y 15/00 257/253 |
| 8,980,667 B2 * | 3/2015 | Cai .......................... G01T 3/08 438/49 |

(Continued)

FOREIGN PATENT DOCUMENTS

| CN | 103675073 A | 3/2014 |
| CN | 104713931 A | 6/2015 |
| CN | 105321995 A | 2/2016 |

*Primary Examiner* — William A Harriston
(74) *Attorney, Agent, or Firm* — Daniel P. Morris, Esq.; Hoffmann & Baron, LLP

(57) ABSTRACT

A biosensor includes a bulk silicon substrate and a vertical bipolar junction transistor (BJT) formed on at least a portion of the substrate. The BJT includes an emitter region, a collector region and an epitaxially grown intrinsic base region between the emitter and collector regions. The biosensor further includes a sensing structure formed on at least a portion of two vertical surfaces of the intrinsic base region of the BJT. The sensing structure includes a channel/trench opening, exposing the intrinsic base region on at least first and second opposing sides thereof, and at least one dielectric layer formed in the channel/trench opening and contacting at least a portion of the intrinsic base region, the dielectric layer being configured to respond to charges in biological molecules.

15 Claims, 18 Drawing Sheets

(51) Int. Cl.
*H01L 29/08* (2006.01)
*H01L 29/10* (2006.01)
*H01L 29/66* (2006.01)
H01L 21/3065 (2006.01)

(52) U.S. Cl.
CPC .... *H01L 29/1004* (2013.01); *H01L 29/66272* (2013.01); *H01L 29/732* (2013.01); *H01L 21/3065* (2013.01)

(56) References Cited

U.S. PATENT DOCUMENTS

| | | | |
|---|---|---|---|
| 9,564,429 B2* | 2/2017 | Cai | H01L 29/1008 |
| 9,625,409 B1* | 4/2017 | Cai | G01N 27/327 |
| 9,726,631 B1 | 8/2017 | Cai et al. | |
| 9,841,398 B2* | 12/2017 | Bustillo | G01N 27/414 |
| 10,332,972 B2* | 6/2019 | Balakrishnan | H01L 29/7327 |
| 10,411,109 B2* | 9/2019 | Reznicek | H01L 29/1004 |
| 2003/0025125 A1* | 2/2003 | Menut | H01L 29/735 257/141 |
| 2006/0125489 A1* | 6/2006 | Feucht | G01N 29/022 324/633 |
| 2015/0108549 A1 | 4/2015 | Benoit et al. | |
| 2016/0379975 A1* | 12/2016 | Cai | H01L 29/0653 257/197 |
| 2019/0157417 A1* | 5/2019 | Balakrishnan | H01L 29/7325 |

\* cited by examiner

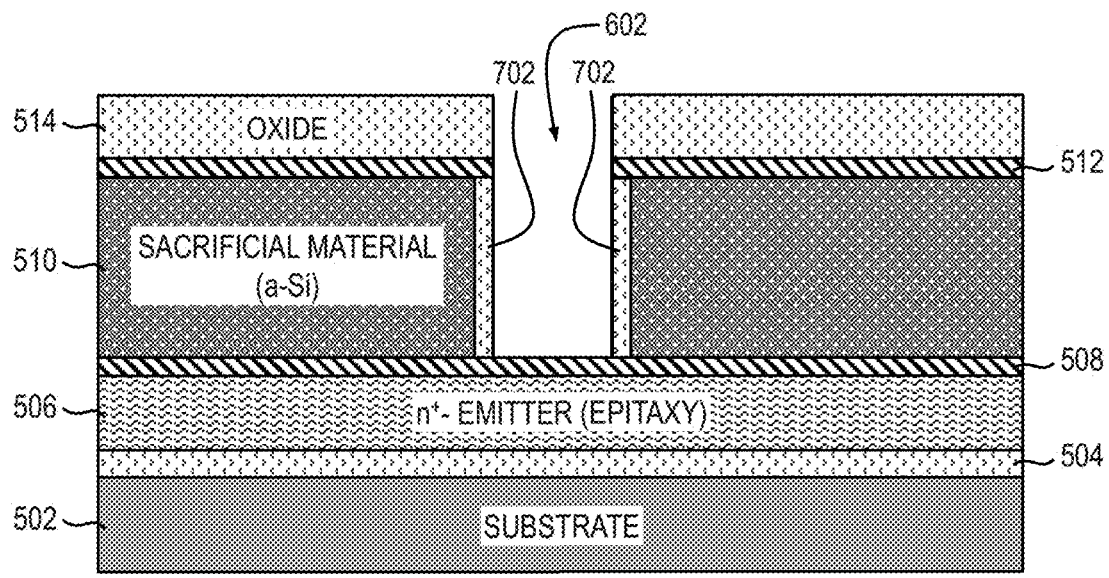
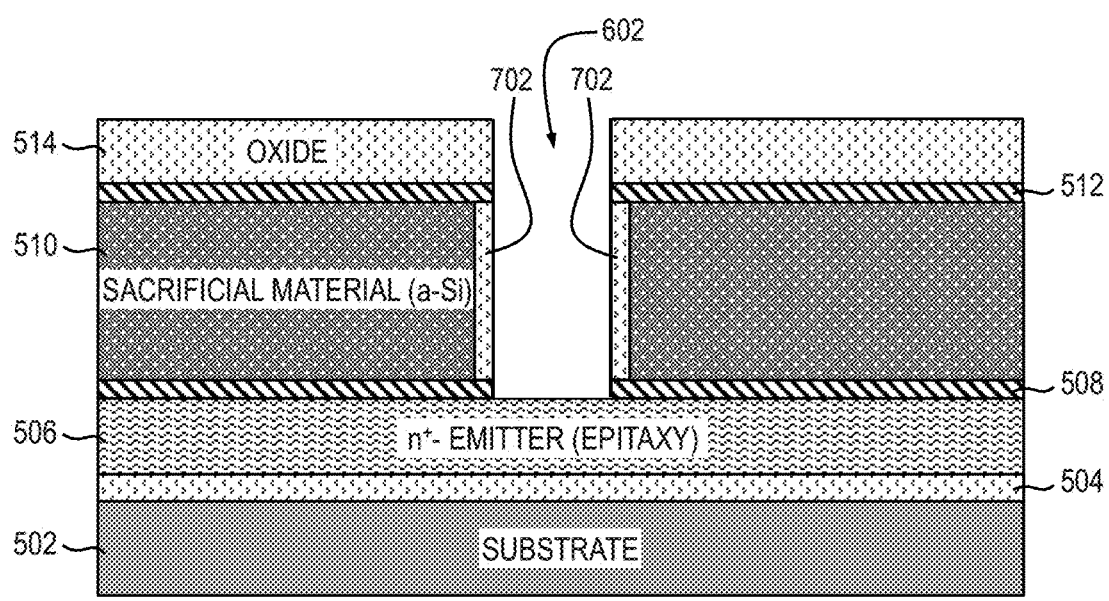

| Tsi(nm) | Q (#/cm2) | NB (/cm3) | Xdep (nm) | Vs (mV) | Jc1/Jc1(0) | Ic(Q)/Ic(0) |
|---|---|---|---|---|---|---|
| 50 | 1.0E+12 | 1.0E+17 | 100 | 1.9E+02 | 2.50E+02 | 250 |
| 50 | 1.0E+12 | 2.0E+17 | 50 | 3.9E+02 | 2.36E+05 | 235545 |
| 50 | 1.0E+12 | 2.5E+17 | 40 | 3.1E+02 | 1.44E+04 | 11534 |
| 50 | 1.0E+12 | 5.0E+17 | 20 | 1.5E+02 | 6.90E+01 | 28 |
| 50 | 1.0E+12 | 1.0E+18 | 10 | 7.7E+01 | 6.44E+00 | 2 |
| 20 | 1.0E+12 | 1.0E+17 | 100 | 3.1E+01 | 1.94E+00 | 2 |
| 20 | 1.0E+12 | 2.5E+17 | 40 | 7.7E+01 | 6.44E+00 | 6 |
| 20 | 1.0E+12 | 5.0E+17 | 20 | 1.5E+02 | 6.90E+01 | 69 |
| 20 | 1.0E+12 | 7.5E+17 | 13 | 1.0E+02 | 1.36E+01 | 9 |
| 20 | 1.0E+12 | 1.0E+18 | 10 | 7.7E+01 | 6.44E+00 | 4 |
| 20 | 1.0E+12 | 2.0E+18 | 5 | 3.9E+01 | 2.33E+00 | 1 |

DUAL SURFACE CHARGE SENSING BIOSENSOR

CROSS-REFERENCE TO RELATED APPLICATIONS

This application claims the benefit of U.S. Provisional Application No. 62/849,033, filed on May 16, 2019, entitled "Dual Surface Charge Sensing Biosensor," which is hereby incorporated by reference herein in its entirety for all purposes.

BACKGROUND

The present invention relates generally to the electrical, electronic and computer arts, and, more particularly, to integrated sensors.

Advancements in microelectronics have facilitated the introduction of numerous applications that improve the quality of life and benefit society in immeasurable ways. In addition to mainstream applications in conventional consumer electronics, microelectronics can be utilized in seemingly remote areas of the population. Given the ever-increasing globalization of society, precise acquisition, real-time (or near real-time) processing and analyses of tremendous amounts of information are in high demand. One example is the use of biosensors that can detect and provide relevant environmental information, such as, but not limited to, radiation levels, inorganic particles, biological entities, etc., to ensure safety, security, and stability of environmental control. In addition, with advancements in mobile technology, technological benefits have been achieved by integrating such biosensors into personal devices to provide real-time and customized readout of information.

Conventionally, different types of biosensors are fabricated for the detection of corresponding different types of materials/substances. For example, Geiger counters are used to detect radiation dose, using ionization produced in a Geiger-Müller tube, and provide a real-time and semi-quantitative readout. However, Geiger counters have limited success in measuring high radiation rates and in measuring the energy of incident radiation. Personal radiation dosimeters in the form of wearable badges and the like are available but cannot provide a real-time indication of radiation; rather, such personal radiation dosimeters provide an indication of accumulated radiation or total radiation dose received. Biosensors, which often combine a biological component with a physicochemical detector, depending on the type of material to be detected, often require a certain amount of time for readout due to the reaction/detection mechanism. Moreover, better resolution/sensitivity requires longer processing time, which sometimes involves special instruments only available in laboratories, thus limiting the portability of biosensors.

SUMMARY

Principles of the invention, as manifested in one or more embodiments thereof, are directed to a monolithic biosensor for detecting the presence of biological entities, and methods for making said biosensor. In one or more embodiments, a biosensor structure is provided that includes embedded fluid channels and a vertically oriented lateral bipolar junction transistor (BJT) device integrated therewith. Such structure preferably utilizes shifts in turn-on voltage of the ideal 60 millivolt (mV)/decade slope of the BJT current-voltage (I-V) curve to achieve detection of charges adjacent to a base area of the BJT device. This novel biosensor structure is capable of sensing both positive and negative surface charges (using NPN and PNP BJTs, respectively) with additional scaling advantages (e.g., by extending the base length). Furthermore, the unique embedded fluid channels can potentially enable detecting trace amounts of charges/substances of interest by its larger liquid containment capacity.

In accordance with an embodiment of the invention, a biosensor for detecting the presence of a biological material includes a bulk silicon substrate, a vertical BJT formed on at least a portion of the substrate, and a sensing structure formed on at least a portion of two vertical surfaces of an intrinsic base of the BJT. The BJT includes an emitter region, a collector region and an epitaxially grown intrinsic base region formed between the emitter and collector regions. The sensing structure includes an opening (e.g., a channel or trench), exposing the intrinsic base region on at least first and second sides, and at least one dielectric layer formed in the opening and contacting at least a portion of the intrinsic base region. The dielectric layer is configured to respond to charges in biological molecules, the charges being converted to a sensing signal by the BJT.

In one or more embodiments, the sensing structure of the biosensor further includes a barrier layer formed on a surface of at least a portion of the dielectric layer. The barrier layer is configured to reduce a drift effect caused by ions from a biological molecule being tested from penetrating into the dielectric layer of the sensing structure.

As used herein, "facilitating" an action includes performing the action, making the action easier, helping to carry the action out, or causing the action to be performed. Thus, by way of example only and without limitation, in the context of a processor-implemented method, instructions executing on one processor might facilitate an action carried out by instructions executing on a remote processor, by sending appropriate data or commands to cause or aid the action to be performed. For the avoidance of doubt, where an actor facilitates an action by other than performing the action, the action is nevertheless performed by some entity or combination of entities.

One or more embodiments of the invention or elements thereof can be implemented in the form of a computer program product including a computer readable storage medium with computer usable program code for performing the method steps indicated. Furthermore, one or more embodiments of the invention or elements thereof can be implemented in the form of a system (or apparatus) including a memory, and at least one processor that is coupled to the memory and operative to perform exemplary method steps. Yet further, in another aspect, one or more embodiments of the invention or elements thereof can be implemented in the form of means for carrying out one or more of the method steps described herein; the means can include (i) hardware module(s), (ii) software module(s) stored in a computer readable storage medium (or multiple such media) and implemented on a hardware processor, or (iii) a combination of (i) and (ii); any of (i)-(iii) implement the specific techniques set forth herein.

Techniques of the present invention can provide substantial beneficial technical effects. By way of example only and without limitation, a biosensor according to one or more embodiments of the invention may provide one or more of the following advantages:
  when NPN and PNP lateral BJT devices are employed, each having their own sensing channels and output (collector) current terminals, capability of detecting both positive and negative charges separately and simultaneously in a common sensing platform;

self-calibrated charge, when the NPN and PNP lateral BJT devices share one sensing channel but have separate output (collector) terminals;

an ability to detect small (e.g., trace) amounts of charges with the advantage of signal amplification and steep threshold slope (60 mV/decade), and preferably engineered NPN and/or PNP lateral BJTs with low (e.g., nearly zero) turn-on voltage (base-emitter voltage, $V_{BE}$).

These and other features and advantages of the present invention will become apparent from the following detailed description of illustrative embodiments thereof, which is to be read in connection with the accompanying drawings.

BRIEF DESCRIPTION OF THE SEVERAL VIEWS OF THE DRAWINGS

The following drawings are presented by way of example only and without limitation, wherein like reference numerals (when used) indicate corresponding elements throughout the several views, and wherein:

FIGS. 5 through 28 are cross-sectional views depicting exemplary processing steps/stages in the fabrication of exemplary biosensors, comprising a vertically oriented lateral BJT structure and dual sensing surfaces, according to embodiments of the present invention;

It is to be appreciated that elements in the figures are illustrated for simplicity and clarity. Common but well-understood elements that may be useful or necessary in a commercially feasible embodiment may not be shown in order to facilitate a less hindered view of the illustrated embodiments.

DETAILED DESCRIPTION

Principles of the present invention will be described herein in the context of illustrative silicon-based biosensors that include a vertical bipolar junction transistor (BJT) device integrally formed with a unique sensing structure. The sensing structure includes embedded fluid channels configured in conjunction with the vertical BJT device to provide a biosensor having dual sensing surfaces. The biosensors according to one or more embodiments are fabricated using a complementary metal-oxide-semiconductor (CMOS) process, thereby allowing the biosensors to be readily integrated with standard CMOS control and/or processing circuitry. It is to be appreciated, however, that the invention is not limited to the specific devices and/or methods illustratively shown and described herein. Rather, aspects of the present disclosure relate more broadly to a monolithic biosensor based on bipolar transistor operation having dual sensing surfaces, and methods for making said biosensor. Moreover, it will become apparent to those skilled in the art given the teachings herein that numerous modifications can be made to the embodiments shown that are within the scope of the claimed invention. That is, no limitations with respect to the embodiments shown and described herein are intended or should be inferred.

Figure 1:
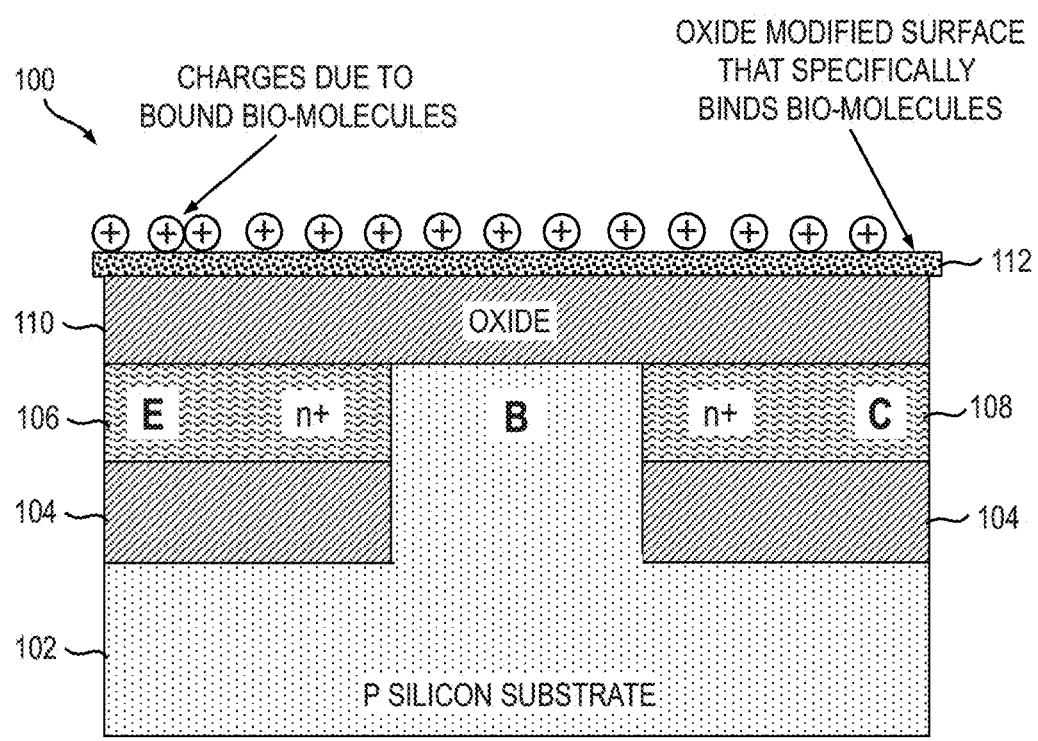
FIG. 1 is a cross-sectional view depicting a standard biosensor based on an inverted lateral bipolar junction transistor (BJT) structure.

FIG. 1 is a cross-sectional view depicting a standard biosensor 100 based on an inverted lateral BJT structure. The biosensor 100 includes a silicon substrate 102 which is doped to be of p-type conductivity. Emitter (E) and collector (C) regions, 106 and 108, respectively, are formed on an insulating layer 104 in defined areas (e.g., wells) in the substrate 102. The emitter and collector regions 106, 108, which are doped to be of n-type conductivity, are separated laterally from one another by a portion of the p-type substrate. The portion of the substrate 102 separating the emitter and collector regions 106, 108 serves as a p-type base (B) which, in conjunction with the n-type emitter and collector regions, forms the lateral BJT structure.

Contact to the p-type base is provided by the p-type substrate 102. Electrical contact to the p-type substrate 102 can be provided via the back-side of the p-type substrate, for the case where the p-type substrate is part of the starting wafer for device fabrication. Alternatively, electrical contact to the p-type substrate can be provided from the front-side via a p-type reach-through region (not explicitly shown) which extends from a top surface of the device structure down to the p-type substrate 102.

The biosensor 100 further includes a planar sensing layer 112 formed on an upper surface of the lateral BJT structure. An oxide layer 110 is formed between the sensing layer 112 and the BJT structure to electrically isolate the BJT structure from the planar sensing layer. The sensing layer 112 comprises an oxide-modified surface which specifically binds bio-molecules. The BJT structure is able to detect charges due to bound bio-molecules present on the sensing layer 112.

Several disadvantages are associated with this biosensor 100. For example, due to the arrangement of the inverted lateral BJT structure, a substrate contact (i.e., contact to p-type substrate 102) is required for setting an emitter-base bias voltage, which significantly limits device density and increases noise due to poor substrate isolation. Additionally, the planar (i.e., flat) shape of the sensing layer 112 renders it difficult to effectively confine biological materials being tested, particularly liquids/droplets. Furthermore, due to the relatively flat shape of the sensing layer 112, only the charge located directly above the base region induces a corresponding image charge in the base, which in turn induces a sensing signal. The charge located directly above the emitter induces a corresponding image charge in the emitter, and the charge located directly above the collector induces a corresponding image charge in the collector. Therefore, the charges located directly above emitter and collector do not contribute to the sensing signal. The planar structure limits scaling of sensing areas for detection of trace amounts of substances being tested/detected in fluids of interest.

Figure 2:
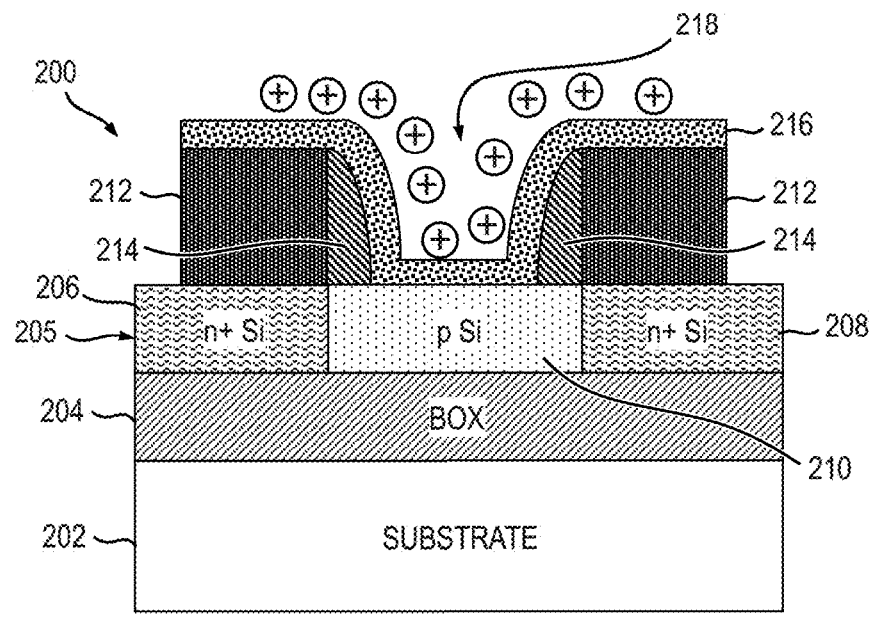
FIGS. 2 and 3 are cross-sectional views depicting exemplary monolithic biosensors including a lateral silicon-on-insulator (SOI) BJT structure.
Figure 3:
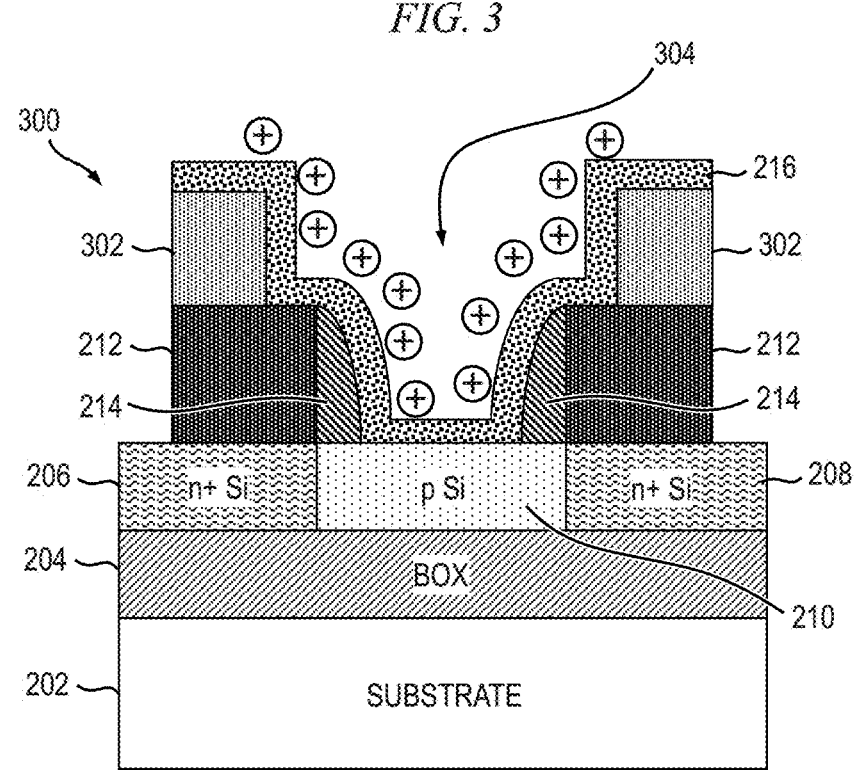

FIGS. 2 and 3 are cross-sectional views depicting monolithic biosensors including a lateral SOI BJT structure. Specifically, with reference to FIG. 2, a biosensor 200 comprises a lateral SOI BJT structure including a substrate 202 on which a buried oxide (BOX) layer 204 is formed. A silicon layer 205, which may be referred to herein as a silicon on insulator (SOI) layer, is formed on an upper surface of the BOX layer 204. Laterally-spaced regions 206 and 208 of n+ conductivity type formed in the SOI layer 205, proximate an upper surface of the SOI layer, form an emitter (E) and a collector (C), respectively, of the SOI BJT structure. A region 210 of p-type conductivity is formed in the upper surface of the SOI layer 205 between the emitter and collector regions 206 and 208. The P region 210, which essentially forms an intrinsic base (B) of the SOI BJT structure, is laterally adjacent to the n+ regions 206, 208 thereby forming respective base-emitter and base-collector p-n junctions.

The biosensor 200 further comprises a sensing structure integrally formed on the upper surface of the BJT structure and electrically coupled with the intrinsic base region 210. The sensing structure includes insulating structures 212 which are formed on the upper surface of the BJT structure, proximate the emitter and collector regions 206, 208. The insulating structures 212 may be formed by patterning an insulating layer, using standard lithographic processing, and etching the insulating layer to define an opening therethrough for exposing the intrinsic base region 210. Dielectric spacers 214 are formed on sidewalls of the insulating structures 212 defining the intrinsic base region opening.

A dielectric layer 216 is deposited on the upper surface of the biosensor 200 (that is, over the insulating structures 212, the sidewall spacers 214 and the exposed intrinsic base region 210). A profile of the dielectric layer 216 is configured to be tapered or "funnel-shaped" by virtue of the insulating structures 212 and spacers 214 upon which the dielectric layer is formed, which beneficially serves as a receptacle 218 (i.e., containing structure) for confining bio-materials being tested/detected (e.g., liquids and/or droplets). The dimensions and shape of the insulating structures 212 and sidewall spacers 214 (e.g., thickness) will determine the profile of the dielectric layer 216, including a depth of the receptacle 218. A surface property of the dielectric layer 216 makes it sensitive to bio-molecules.

Charges generated by bound bio-molecules located directly above the intrinsic base region 210, including those charges located on the part of the modified dielectric layer 216 on the spacer 214, induce corresponding image charges in the intrinsic base region, resulting in an increase in the electron current flowing from the emitter 206 to the collector 208. The charges generated by bound bio-molecules located elsewhere, for example above emitter 206 and/or collector 208, are generally too far away from the intrinsic base region 210 to contribute effectively to the electron current flowing from emitter 206 to collector 208. The charges generated by bound bio-molecules located on the top dielectric layer form image charges in the electrically conductive middle layer, which in turn form corresponding image charges in the intrinsic base region 210.

FIG. 3 is a cross-sectional view depicting another biosensor 300 including a lateral SOI BJT structure. The biosensor 300 is formed in manner consistent with the biosensor 200 shown in FIG. 2, except that the biosensor 300 includes a sensing structure that is modified slightly compared to the sensing structure of the biosensor 200 of FIG. 2. Specifically, with reference to FIG. 3, the sensing structure of the biosensor 300 includes second insulating structures 302 formed on at least a portion of the upper surface of the insulating structures 212. This second level of insulating structures 302 results in a dielectric layer 216 that exhibits a more stepped profile and a deeper receptacle 304 for confining a larger volume of bio-molecules being tested.

Several disadvantages are associated with the biosensors 200 and 300. For example, the planar (i.e., flat) structure limits scaling of the sensing areas for detection of trace amounts of substances to be tested/detected in fluids of interest. Furthermore, fluid confinement on the upper surface of the biosensors 200, 300 limits integration capability with peripheral electronics if needed.

Figure 4A:
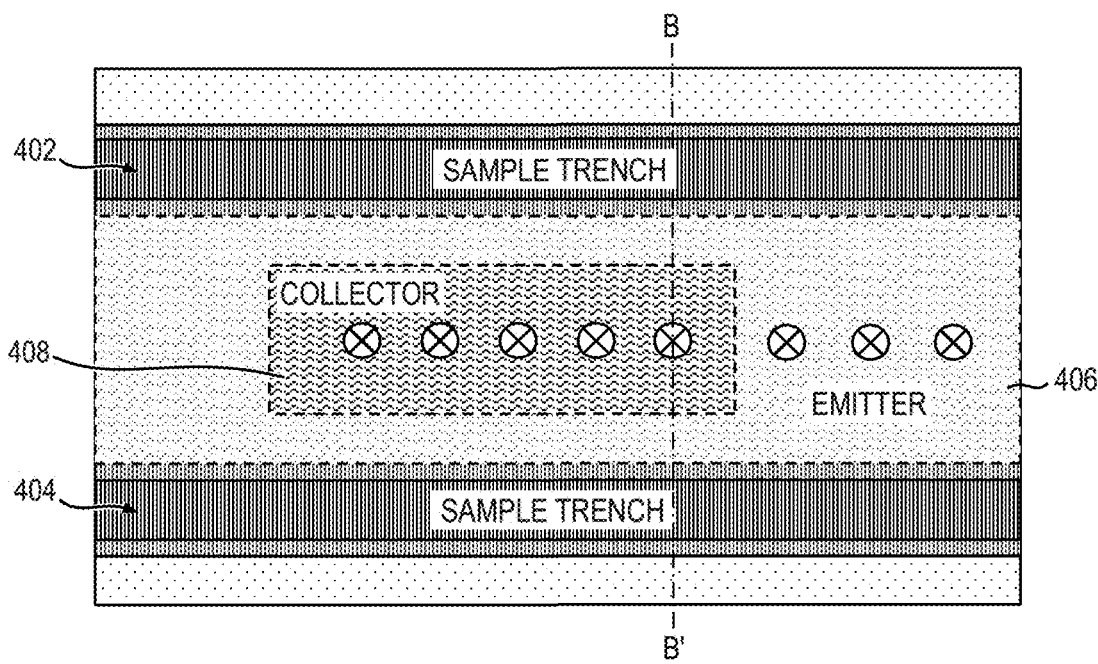
FIGS. 4A and 4B are top plan and cross-sectional views, respectively, depicting at least a portion of an exemplary monolithic biosensor including dual surface charge sensing, according to an embodiment of the present invention.
Figure 4B:
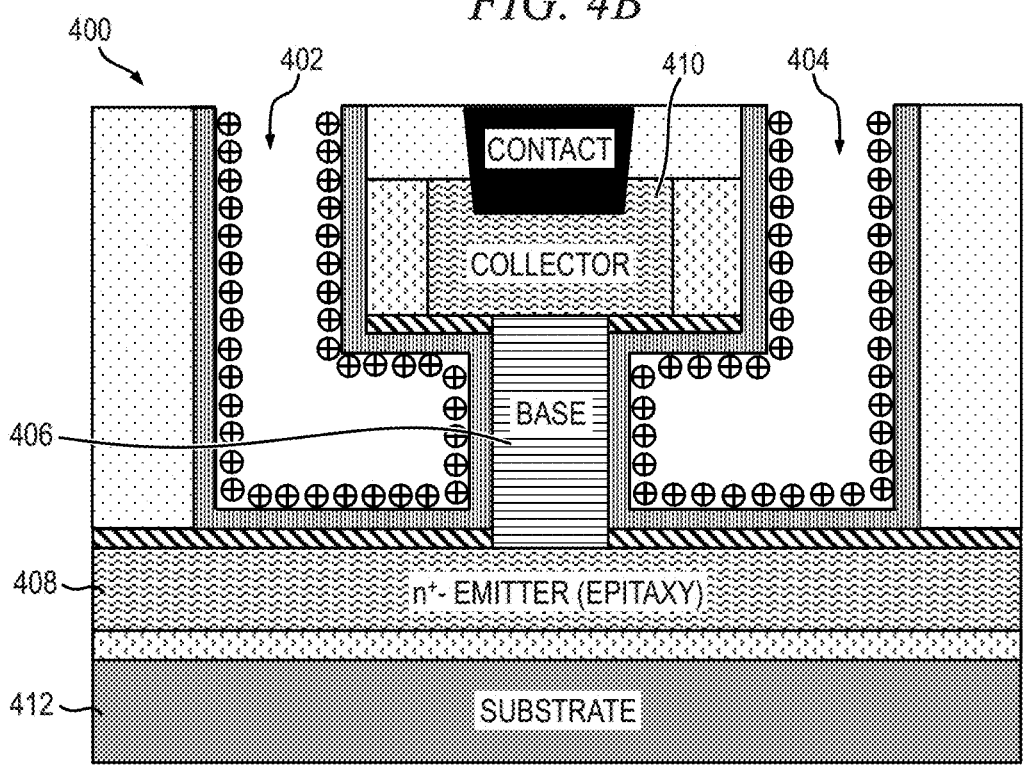

FIGS. 4A and 4B depict at least a portion of an exemplary monolithic biosensor 400 including dual surface charge sensing, according to an embodiment of the invention; FIG. 4A is a top plan view of the biosensor and FIG. 4B is a cross-sectional view of the biosensor taken along line B-B' in FIG. 4A. The biosensor 400 includes a vertically oriented lateral BJT device and a sensing structure which includes multiple (e.g., two in this example) embedded fluid channels 402 and 404. Although two fluid channels are shown in FIG. 4A, it is to be appreciated that embodiments of the invention are not limited to two channels. The fluid channels 402, 404 are preferably formed so as not to extend above a planar upper surface of the structure, but are instead adapted to convey a fluid to be tested/detected below the upper surface of the biosensor 400 and proximate to opposing vertical sidewalls of a base region 406 of the BJT device. The base region 406 of the BJT device, which, in one or more embodiments, is epitaxially formed, is disposed between an underlying emitter region 408 and an overlying collector region 410. The BJT device and sensing structure are integrated on a common substrate 412 as shown.

The biosensor structure beneficially utilizes shifts in turn-on voltage (i.e., base-emitter voltage, $V_{BE}$) of an ideal 60 mV/decade slope of BJT current-voltage curve to achieve detection of charges adjacent to the base region of the BJT. Although the illustrative biosensor 400 shown in FIGS. 4A and 4B utilizes an NPN BJT device, it is to be understood that the BJT structure may, in other embodiments, comprise an NPN and/or a PNP BJT device. Such a BJT device structure is capable of sensing both positive and negative surface charges (via NPN and PNP BJT devices, respectively). Furthermore, in embodiments utilizing both NPN and PNP BJT devices, each having their own sensing channel and output (collector) current terminal, the biosensor 400 functions as one common sensing platform that is adapted to advantageously detect both positive and negative charges separately and simultaneously.

Figure 4C:
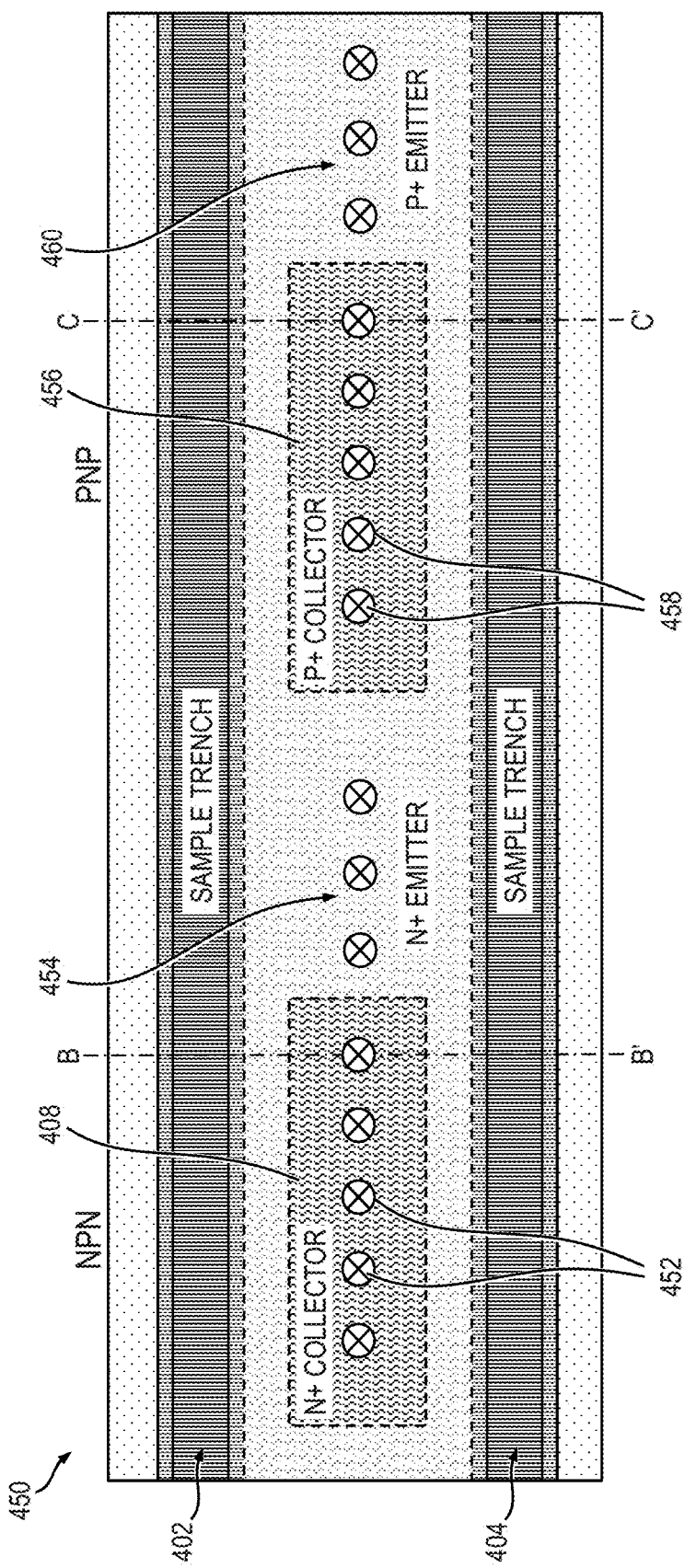
FIG. 4C is a top plan view depicting at least a portion of an exemplary monolithic biosensor including dual surface charge sensing using both NPN and PNP vertically oriented lateral BJT devices, according to an embodiment of the present invention.

FIG. 4C is a top plan view depicting at least a portion of an exemplary monolithic biosensor 450 including dual surface charge sensing using both NPN and PNP BJT devices, according to an embodiment of the invention. The dual-BJT biosensor 450 includes two embedded fluid channels 402 and 404 and NPN and PNP vertically oriented lateral BJT devices formed adjacent to one another along the channels 402, 404. Specifically, the NPN BJT device includes an N+ collector region 408 and corresponding collector contacts 452, and an N+ emitter region 454 and corresponding emitter contacts. Likewise, the PNP BJT device includes a P+ collector region 456 and corresponding collector contacts 458, and an N+ emitter region 460 and corresponding emitter contacts. A cross-section of the PNP BJT device portion of the biosensor 450 taken along line C-C', illustrating an exemplary fabrication of the intrinsic base region of the BJT device and embedded fluid channels 402, 404, will be essentially the same as the illustrative cross-sectional view shown in FIG. 4B, except that the conductivity types (N or P) of the respective materials forming the collector, intrinsic base and emitter regions will be reversed, as will become apparent to those skilled in the art.

Additionally, the NPN and PNP BJT devices should be electrically isolated from one another, and are processed using multiple masks. In one or more embodiments, the biosensor 450 preferably includes a separating area formed between the NPN and PNP BJT devices, such as, for example, a shallow trench isolation (STI) region. Those skilled in the art will know how to form an STI or similar isolation region.

In one or more embodiments, the separate NPN and PNP vertically oriented lateral BJT devices share one sensing channel but have separate output (collector) current terminals, which provides self-calibrated charge sensing. For example, when there are certain amounts of positive charges in the tested fluid channel, the NPN vertically oriented lateral BJT device will have a lower turn-on ($V_{BE}$) voltage that leads to higher output (collector) current ($I_{C\_NPN}$) with the same $V_{BE}$ without any charges in the channel, while the PNP vertically oriented lateral BJT device will have a lower $I_{C\_PNP}$. The precise amount/density of charges in the fluid can be obtained/calibrated by comparing the charges calculated from $\Delta I_{C\_NPN}$ and $\Delta I_{C\_PNP}$ (or by comparing $\Delta V_{BE\_NPN}$ and $\Delta V_{BE}$ to maintain the same level of $I_{C\_NPN}$ and $I_{C\_PNP}$).

By way of example only and without limitation, FIGS. 5 through 28 are cross-sectional views depicting exemplary processing steps/stages in the fabrication of an exemplary biosensor 500, comprising a vertically oriented lateral NPN BJT, according to embodiments of the invention. Although the overall fabrication method and the structures formed thereby are entirely novel, certain individual processing steps required to implement the method may utilize conventional semiconductor fabrication techniques and conventional semiconductor fabrication tooling. These techniques and tooling will already be familiar to one having ordinary skill in the relevant arts given the teachings herein. Moreover, many of the processing steps and tooling used to fabricate semiconductor devices are also described in a number of readily available publications, including, for example: P. H. Holloway et al., Handbook of Compound Semiconductors: Growth, Processing, Characterization, and Devices, Cambridge University Press, 2008; and R. K. Willardson et al., Processing and Properties of Compound Semiconductors, Academic Press, 2001, which are both hereby incorporated herein by reference in their entireties for all purposes. It is emphasized that while some individual processing steps are set forth herein, those steps are merely illustrative, and one skilled in the art may be familiar with several equally suitable alternatives that would also fall within the scope of the invention.

It is to be appreciated that the various layers and/or regions shown in the accompanying figures may not be drawn to scale. Furthermore, one or more semiconductor layers of a type commonly used in such integrated circuit devices may not be explicitly shown in a given figure to facilitate a clearer description. This does not imply that the semiconductor layer(s) not explicitly shown are omitted in the actual integrated circuit device.

Figure 5:
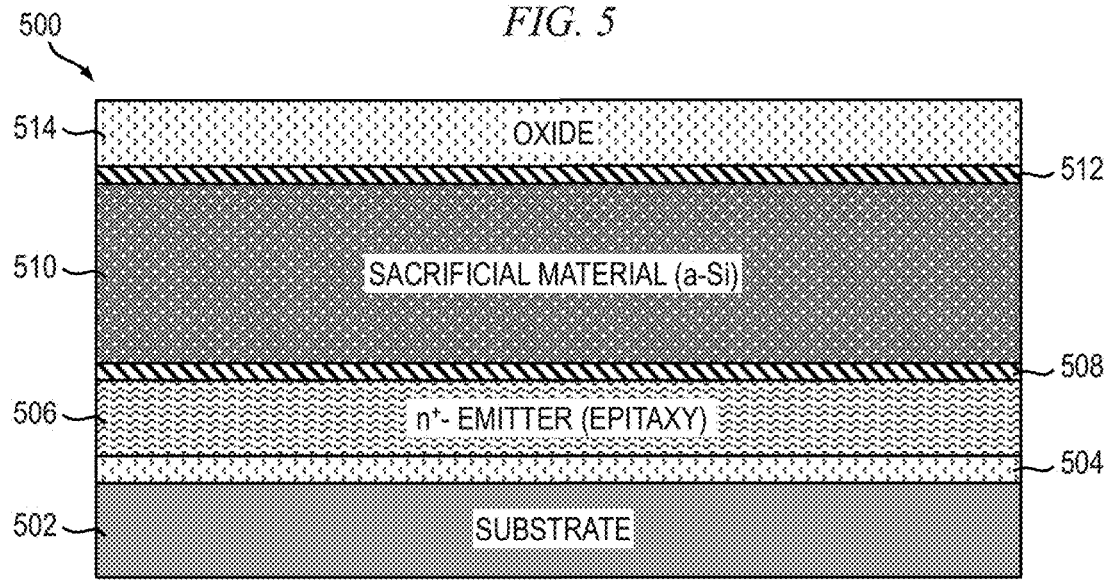

With reference to FIG. 5, a punch-through stop (PTS) layer 504 is formed on a semiconductor substrate 502. The substrate 502 may comprise, for example, silicon, although embodiments of the invention are not limited to any particular material. The PTS layer 504 in one or more embodiments is formed of a dielectric material, preferably an oxide, such as, for example, silicon dioxide ($SiO_2$), and serves, at least in part, to electrically isolate the subsequently formed BJT device from the underlying substrate 502. It is to be understood that in the context of an SOI wafer, like that shown in FIG. 5, the isolation is provided by the SOI BOX layer. Alternatively, if the biosensor 500 is formed on a bulk substrate rather than an SOI wafer, the PTS layer 504 may comprise a semiconductor layer doped with an impurity having a conductivity type (e.g., N or P) which is opposite to that of the substrate. A bottom (emitter) epitaxy layer 506 is formed on at least a portion of an upper surface of the PTS layer 504. In one or more embodiments, the emitter epitaxy layer 506 is highly doped to a prescribed doping concentration (e.g., $10^{16}$ to $10^{21}$ $cm^{-3}$) with an n-type dopant, such as, for example, phosphorus (P) or arsenic (As), using a known doping process (e.g., ion implantation). In other embodiments, such as when forming a PNP BJT device, a p-type dopant of a prescribed doping concentration may be used to form the emitter epitaxy layer 506.

A blanket bottom spacer 508 (e.g., nitride) is formed on at least a portion of an upper surface of the emitter epitaxy layer 506. A sacrificial placeholder material layer 510, for example amorphous silicon (a-Si) is formed on at least a portion of an upper surface of the bottom spacer 508, and a top spacer 512 is then formed on at least a portion of an upper surface of the sacrificial material layer 510. The bottom and top spacers 508 and 512, respectively, may be formed of an insulating material, such as a nitride (e.g., silicon nitride), although embodiments of the invention are not restricted to any specific material(s). Furthermore, the bottom and top spacers 508, 512 need not be formed of the same material. A dielectric layer 514, preferably an oxide (e.g., $SiO_2$), is formed on an upper surface of the top spacer 512, as shown.

Figure 6:
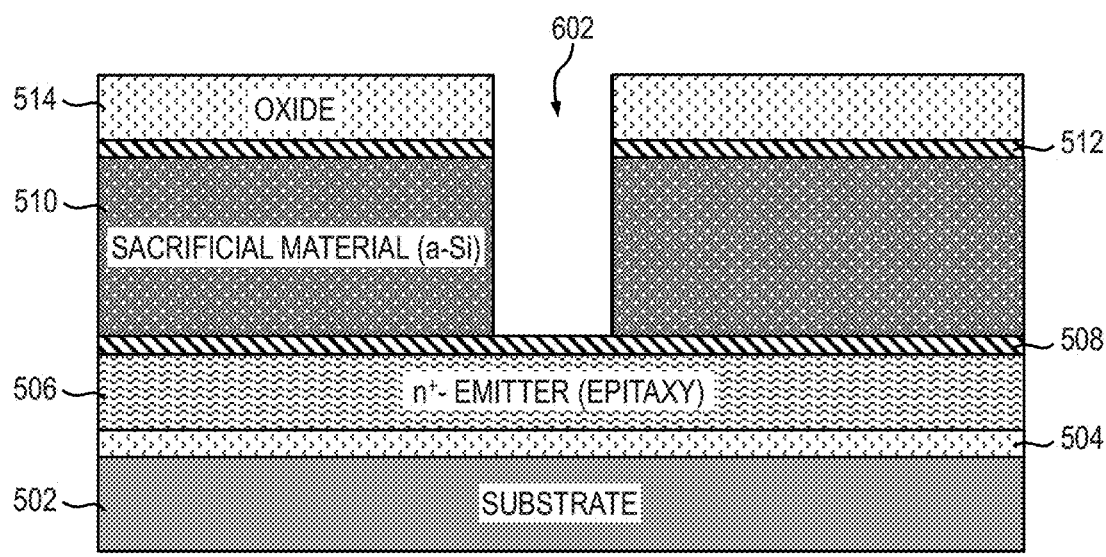

FIG. 6 depicts an etching step for forming a substantially vertical trench 602 or other opening through a selected portion of the oxide layer 514, top spacer layer 512 and sacrificial placeholder material (a-Si) layer 510, selective to the bottom spacer layer 508. Thus, a portion of the bottom spacer layer 508 is exposed through the opening in trench 602. The trench opening may be formed, for example, using reactive ion etching (RIE), or another suitable etching process, as will be known by those skilled in the art. This opening 602 will be used to contain a base region of the BJT structure formed in a subsequent processing step, as will be described in further detail herein below.

In FIG. 7, dielectric spacers 702 (e.g., oxide) are formed on sidewalls of at least the sacrificial placeholder material layer 510 which is exposed in the trench 602. The dielectric spacers 702 are preferably formed using plasma or any other method of oxidation, or very thin oxide formation on dummy polysilicon, as will be known by those skilled in the art.

In FIG. 8, a portion of the bottom spacer layer 508 forming a bottom wall of the trench 602 is removed, such as by etching selective to the doped bottom compound semiconductor material, to thereby expose the doped emitter epitaxy layer 506 through the trench opening.

Figure 9:
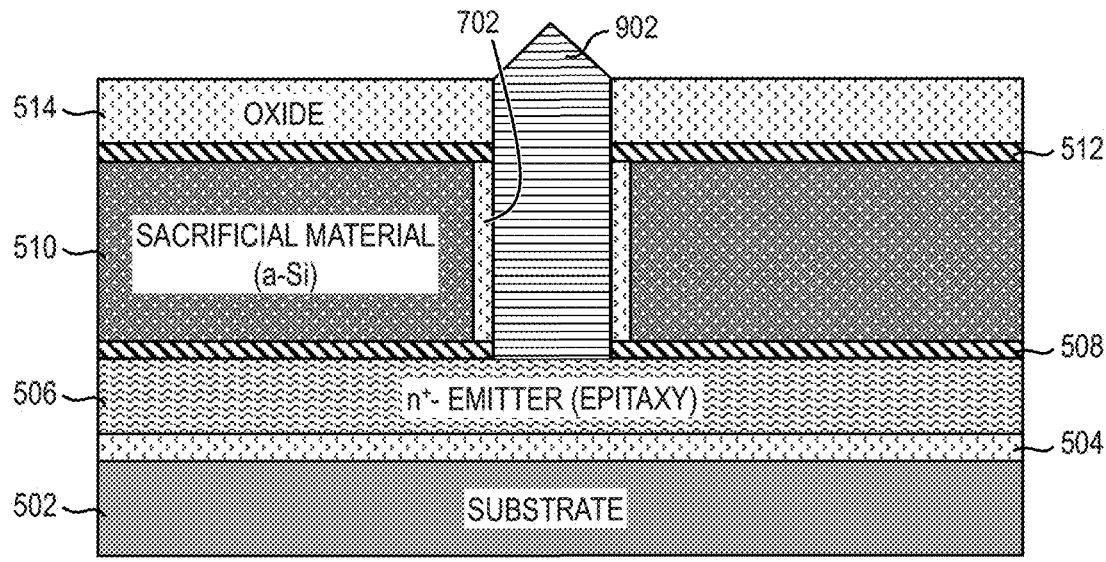
Figure 10:
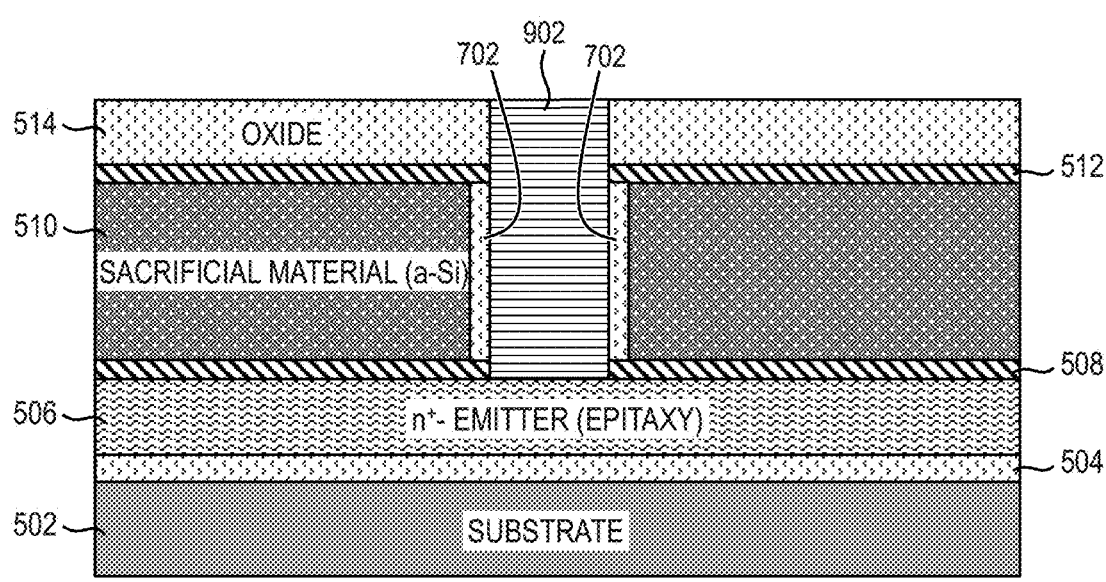

With reference to FIG. 9, an epitaxial growth of base material is performed which will form a base region 902 of the NPN BJT device. The base region 902, in this exemplary embodiment, comprises material that is doped with p-type material, and thus forms a P-N junction with the underlying n+ emitter epitaxy layer 506, which electrically contacts the base region. In alternative embodiments in which a PNP BJT device is formed, the base region 902 comprises material doped with n-type material and forms a P-N junction with the underlying p+ emitter epitaxy layer. An upper surface of the structure is then planarized, such as by using a chemical mechanical polishing (CMP) process or the like, as shown in FIG. 10. After CMP, the epitaxial overgrowth of the base region 902 protruding above an upper surface of the structure is removed so that the base region is substantially planar with the oxide layer 514.

Figure 11:
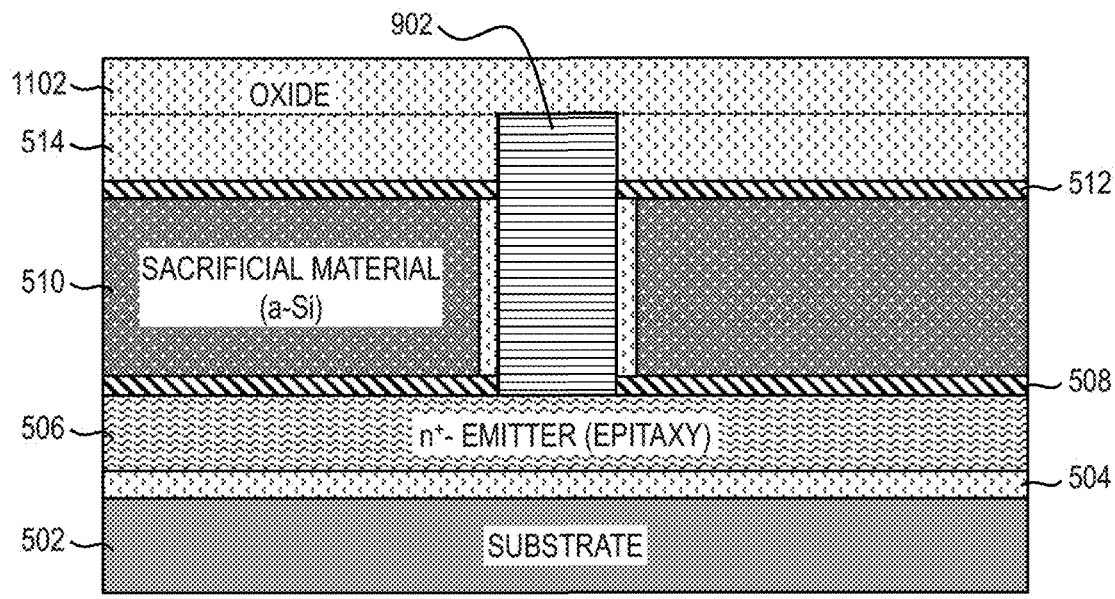
Figure 12:
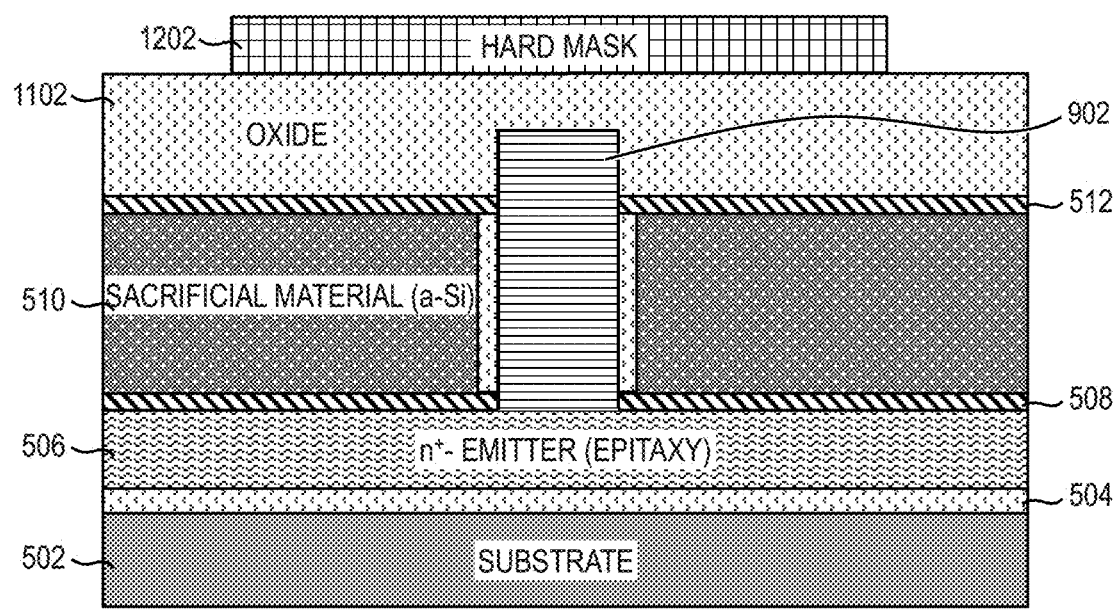
Figure 13:
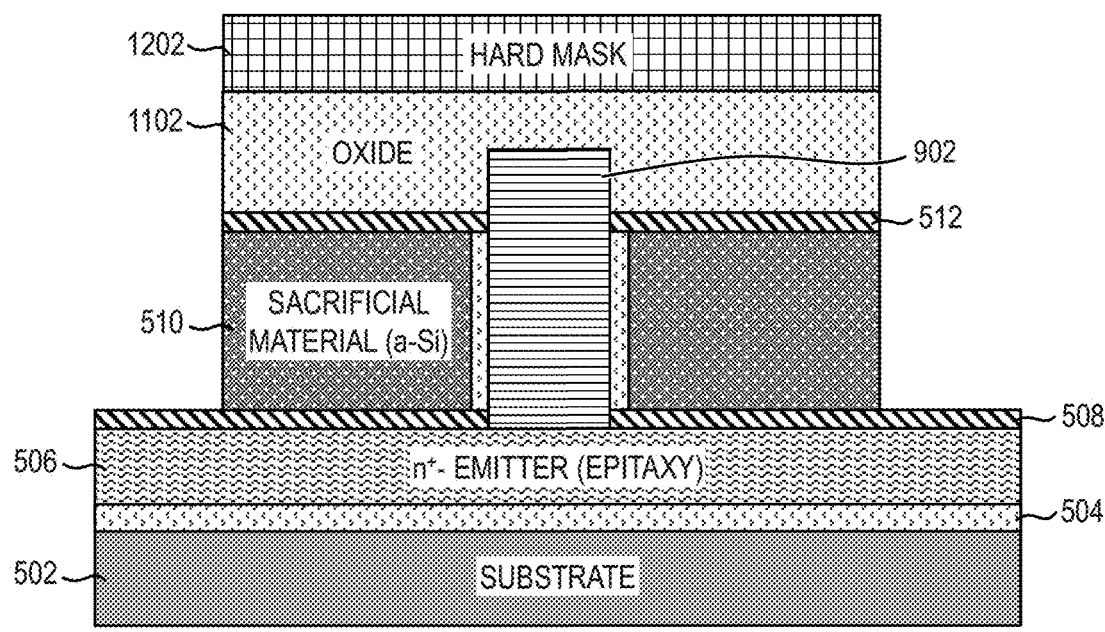

As shown in FIG. 11, an oxide layer 1102, or other dielectric layer, is formed over at least a portion of the upper surface of the structure (e.g., over the oxide layer 514 and base region 902), such as by an oxide deposition process. The oxide layer 1102, which in some embodiments is comprised of the same material (e.g., $SiO_2$) as that used to form the underlying oxide layer 514, is then preferably planarized (e.g., using CMP or the like). A trench-defining hard mask layer 1202 is then formed on at least a portion of the upper surface of the oxide layer 1102, as depicted in FIG. 12. The hard mask layer 1202 can be formed using standard photolithographic patterning, as will be known by those skilled in the art. Using the hard mask layer 1202, unprotected portions of the oxide layer 1102/514, top spacer layer 512 and sacrificial placeholder material layer 510 are etched down to the bottom spacer layer 508, such as, for example, using RIE or similar, as shown in FIG. 13.

Figure 14:
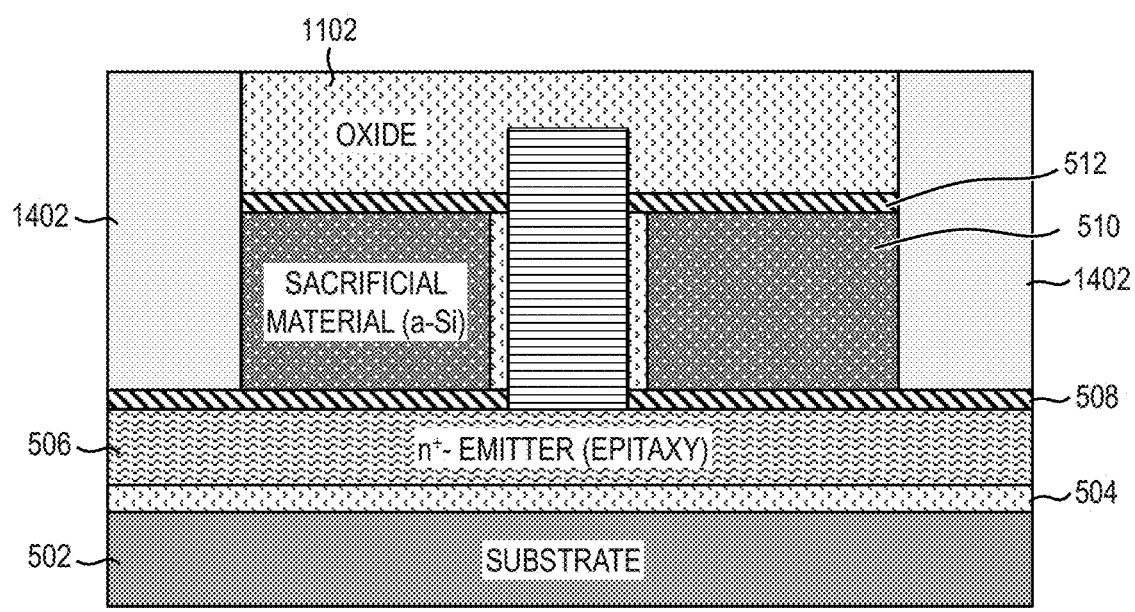
Figure 15:
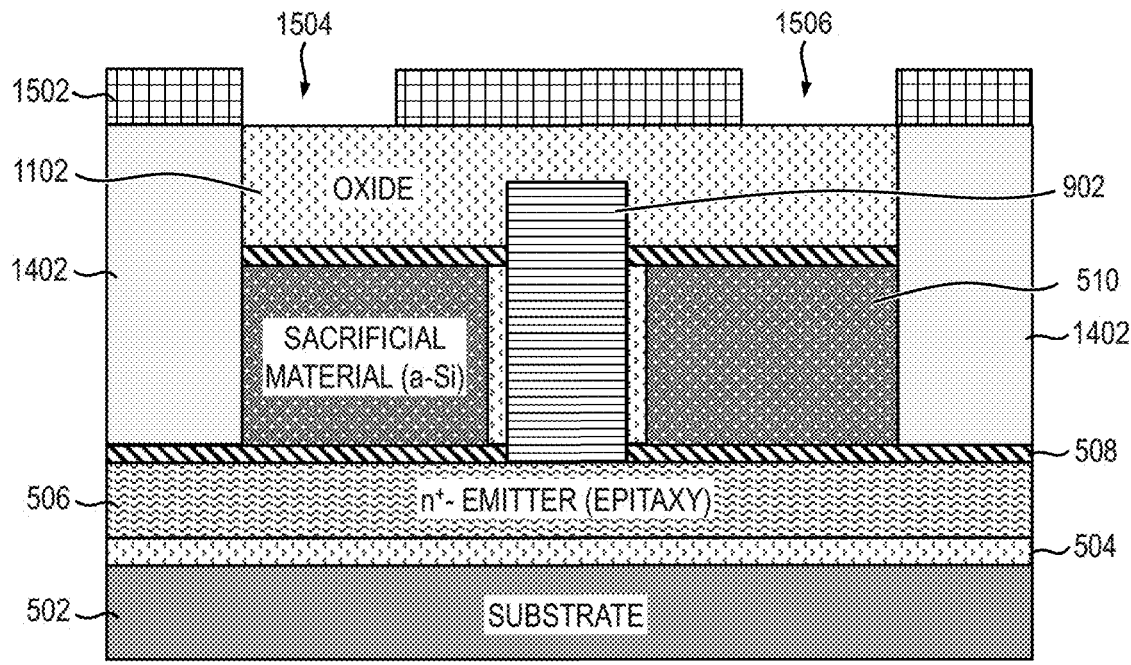

With reference to FIG. 14, the trench-defining hard mask layer 1202 is removed and the an insulating material layer 1402, such as an interlayer dielectric (ILD) material layer, is formed over the structure. The insulating material layer 1402 may be formed using a known oxide deposition technique (e.g., atomic layer deposition (ALD), chemical vapor deposition (CVD), etc.) to fill in gaps in the structure, such as on sidewalls of the sacrificial placeholder material layer 510, top spacer layer 512 and oxide layer 1102. CMP is preferably performed to planarize the structure. Next, a hard mask layer 1502 is formed in a select pattern on the upper surface of the structure, as shown in FIG. 15. The hard mask layer 1502 preferably covers the underlying base region 902, overlapping a prescribed amount on each side of the base region, and trench outside. Alignment is not really an issue since device dimensions and trench size are on the order of about 100 nanometers (nm) to several micrometers (μm). Openings 1504 and 1506 in the hard mask layer 1502, exposing the underlying oxide layer 1102, will be used in a subsequent processing step to define fluid channels (e.g., 402, 404 in FIG. 4B) which form a portion of the sensing structure in the completed biosensor device.

Figure 16:
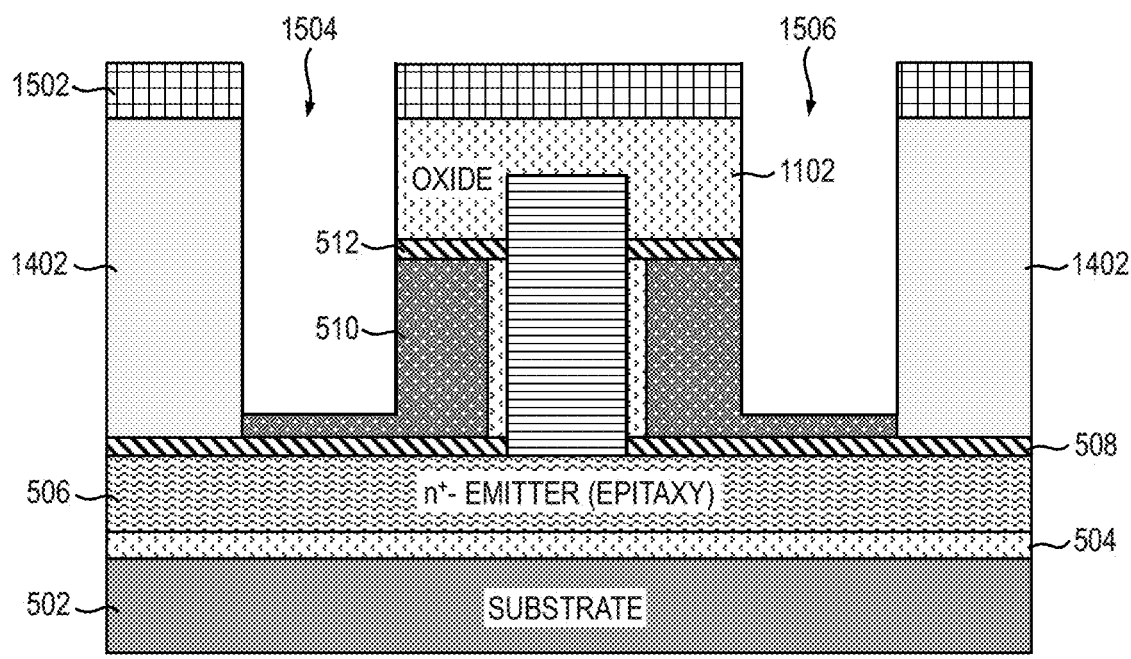
Figure 17:
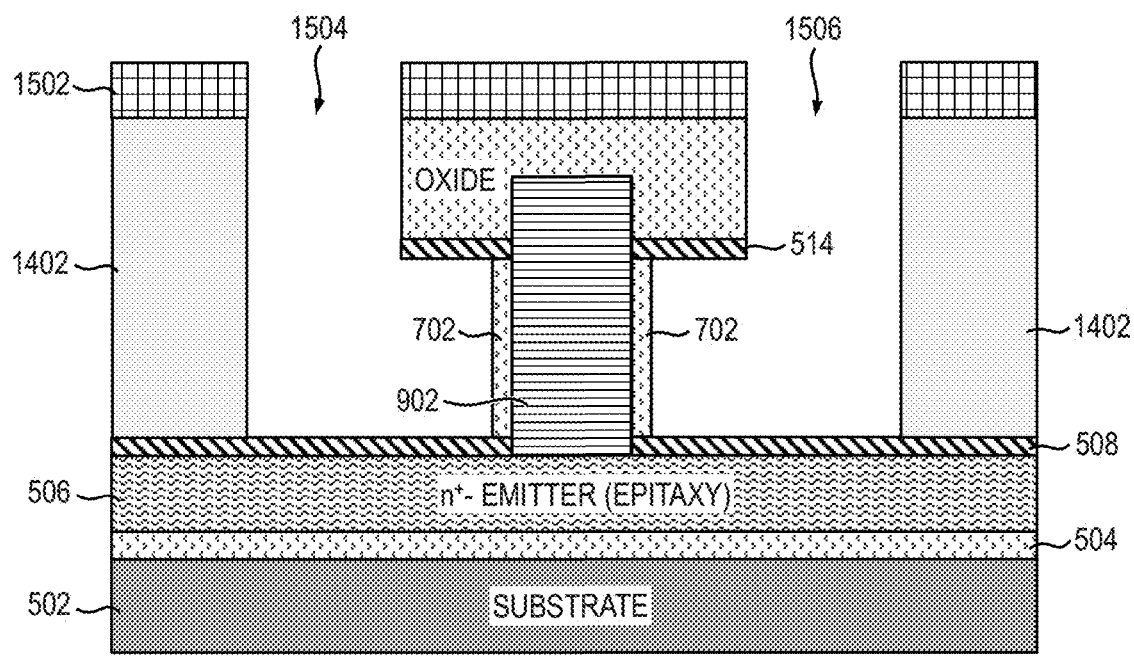
Figure 18:
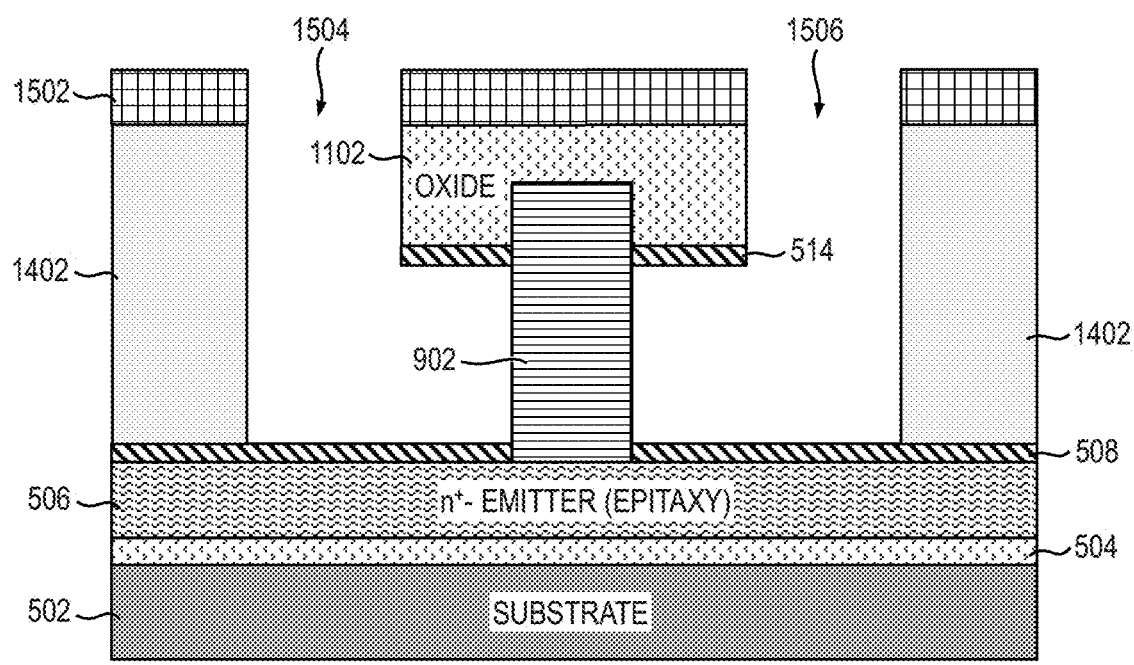

In FIG. 16, the structure 500 is etched to remove portions of the oxide layer 1102, top spacer layer 512 and a portion of the sacrificial placeholder material layer 510 not protected by the hard mask. In one or more embodiments, RIE is used to expose the oxide layer 1102, top spacer layer 512 and sacrificial material layer 510; etching is stopped close to a bottom of the sacrificial material layer 510/bottom spacer layer 508 interface, leaving at least a thin portion (e.g., 10 nm) of the sacrificial material layer exposed at the bottom of the openings 1504, 1506. It is to be appreciated that the thickness of the remaining sacrificial material layer 510 is not critical; the primary objective is to etch through the oxide layer 1102 and top spacer layer 512 to thereby expose the sacrificial material layer 510. The RIE can be selective to the material used for layer 510, such that substantially no sacrificial material layer 510 is removed, or the RIE can be non-selective, in which case etching would be closely monitored and halted once the sacrificial layer 510 is exposed. The sacrificial placeholder material layer 510 is then removed, leaving the base region 902 and thin sidewall dielectric spacers 702 separating two trenches/channels 1504, 1506, as shown in FIG. 17.

The two channels 1504, 1506 in this illustrative embodiment are defined by the space enclosed by hard mask layer 1502, insulating material layer 1402, oxide layer 1102, top spacer layer 514, sidewall dielectric spacers 702, and bottom spacer layer 508. The dielectric spacers 702 surrounding the base region 902 are then removed, such as, for example, using a short hydrofluoric acid (HF) etch or SiCoNi, with the resulting structure depicted in FIG. 18.

Figure 19:
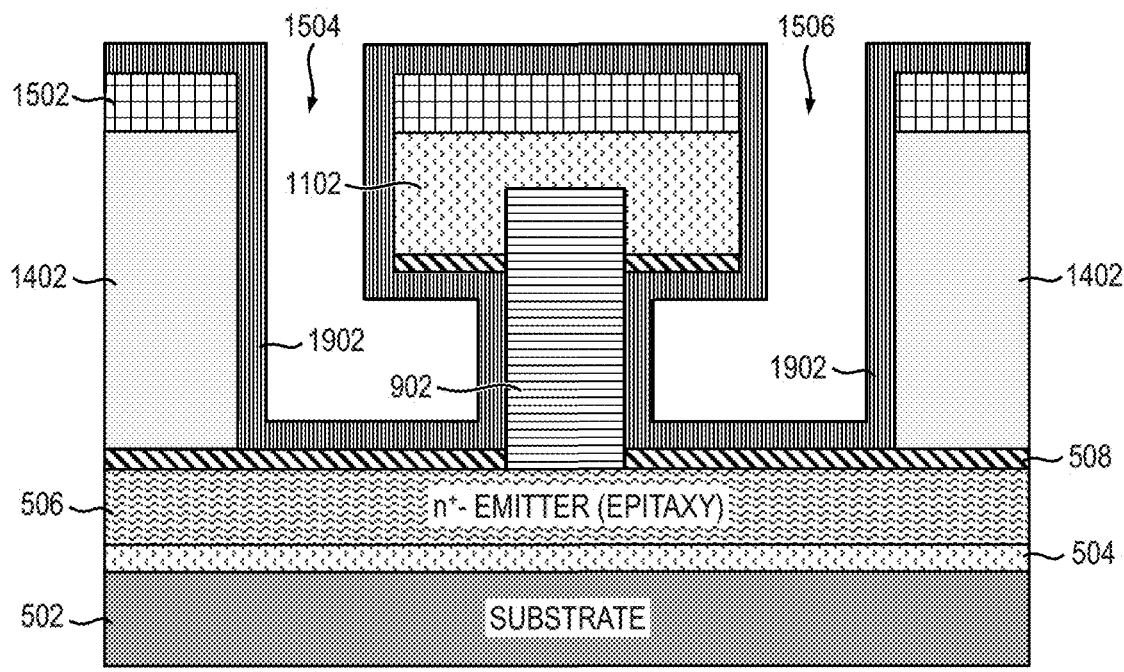
Figure 20:
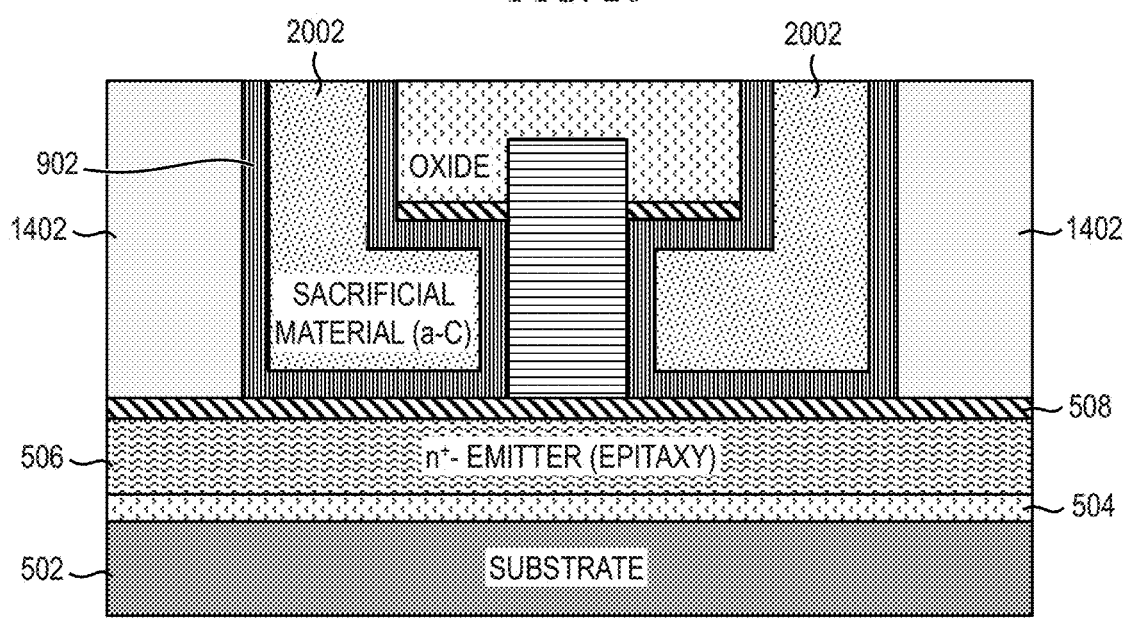

In FIG. 19, a dielectric (e.g., oxide) layer 1902 is formed over the upper surface of the structure and lining the interior walls of the channels 1504, 1506. Specifically, the dielectric layer 1902 is at least formed on the hard mask layer 1502, insulating material layer 1402, oxide layer 1102, top spacer layer 514, sidewall dielectric spacers 702, and bottom spacer layer 508, defining an interior space of the channels 1504, 1506. This dielectric layer 1902 will subsequently be modified to have a surface that specially bonds to bio-molecules. The channels 1504, 1506 are then filled with a sacrificial material 2002 (e.g., a-Si, amorphous carbon (a-C), silicon carbide (SiC), SiCO, etc.), and CMP or alternative planarization process is performed to remove the hard mask layer 1502 and to planarize the upper surface of the structure, as shown in FIG. 20.

Figure 21:
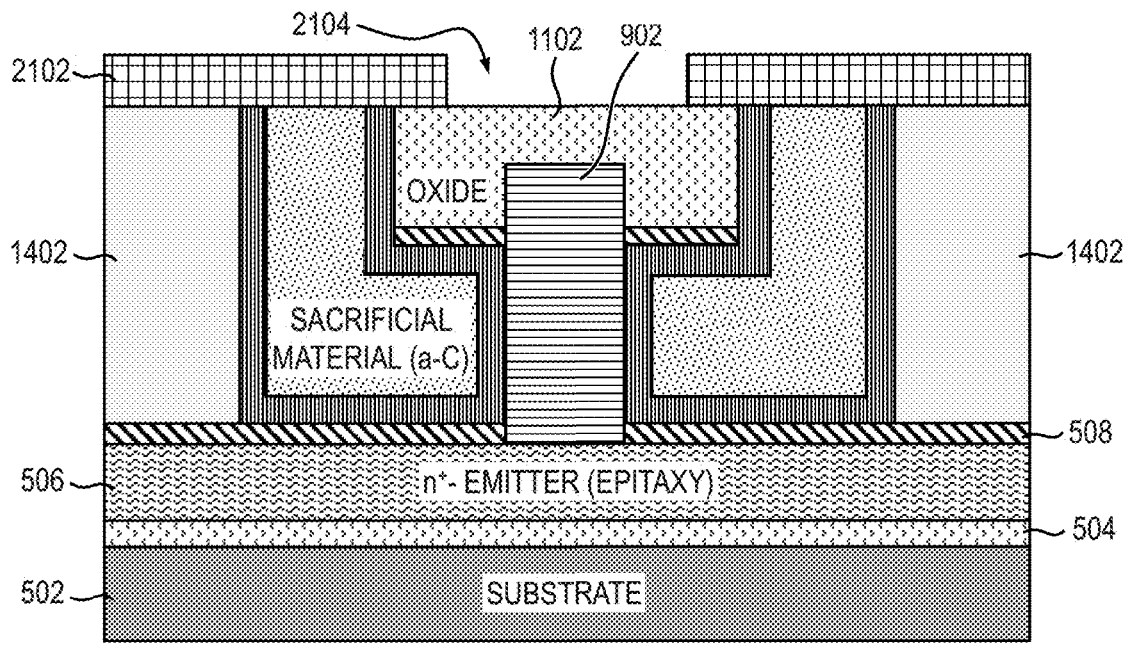

With reference now to FIG. 21, a hard mask layer 2102 is formed on at least a selected portion of the upper surface of the structure. The hard mask layer 2102 is preferably formed in a select pattern, including at least one opening 2104 therein that is preferably aligned with (e.g., centered over) and slightly larger than the base region 902, overlapping a prescribed amount on each side of the base region. This opening 2104 in the hard mask layer 2102 will be subsequently used to form a collector region of the BJT device, as will be described in further detail herein below.

Figure 22:
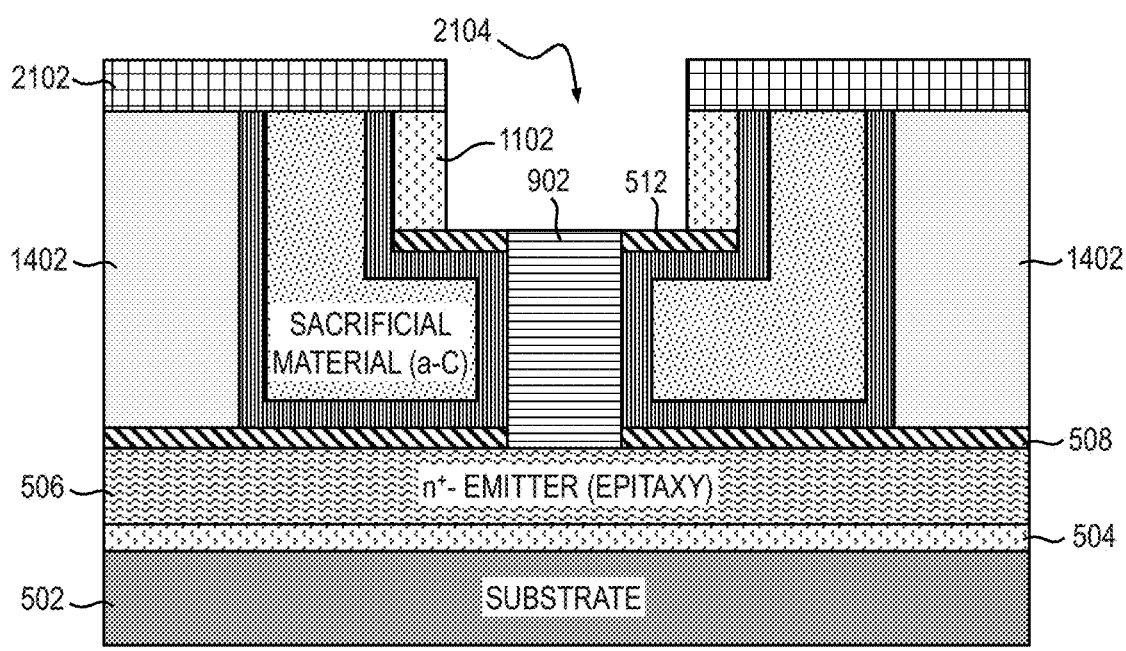
Figure 23:
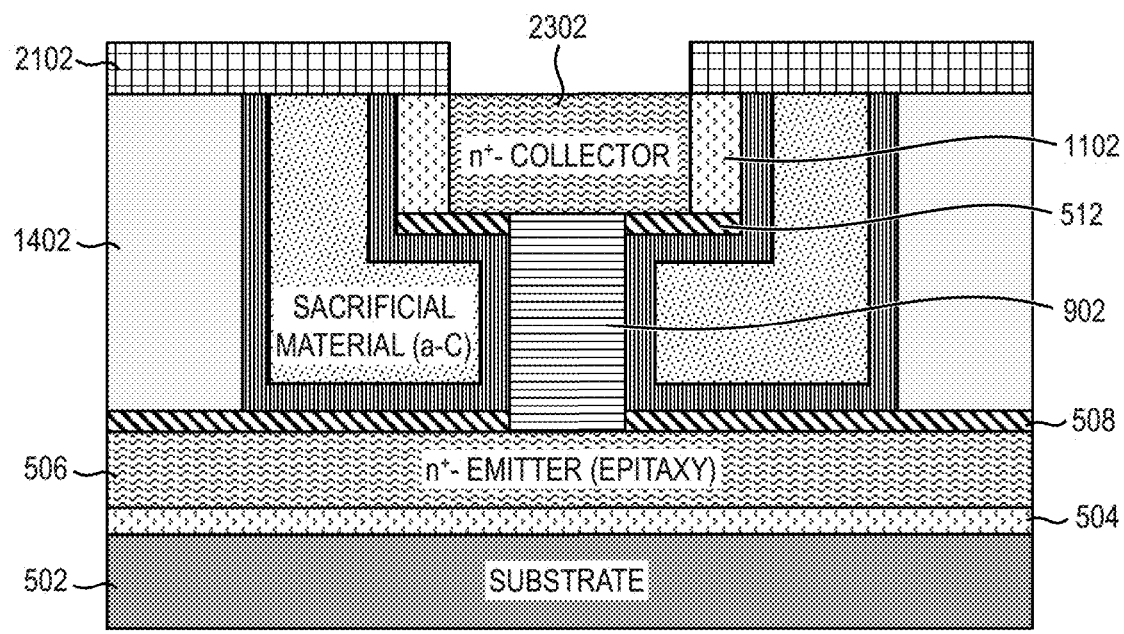
Figure 24:
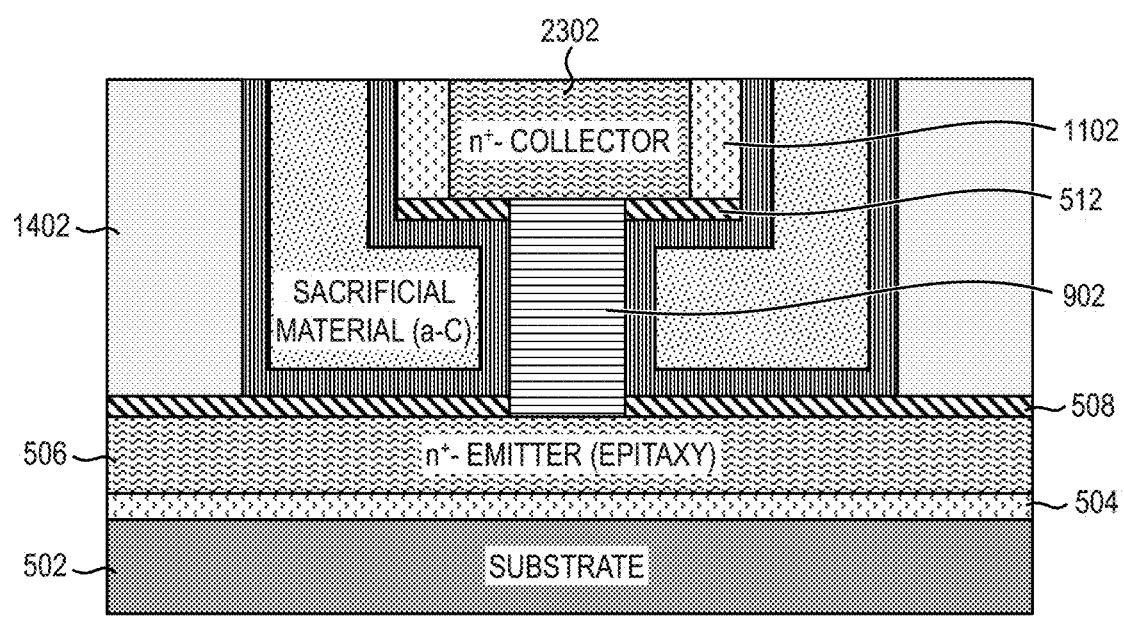

In FIG. 22, a portion of the oxide layer 1102 exposed in the opening 2104 through the hard mask layer 2102 is recessed, such as by an etching process (e.g., RIE), along with an upper portion of the base region 902, down to the top spacer layer 512. A collector region 2302 is formed within a cavity defined by oxide layer 1102 sidewalls and a bottom formed by a portion of the top spacer layer 512 and the upper surface of the base region 902, as shown in FIG. 23. The collector region 2302, in one or more embodiments, is formed by epitaxial growth of collector material, which preferably comprises epitaxy or large grain polysilicon (which is defective epitaxy); defects will not propagate into the base epitaxy region 902 used as a seed layer. The collector material is preferably highly doped with n-type material so as to form a P-N junction with the underlying p-type base region 902. In one or more alternative embodiments in which a PNP BJT device is formed, the collector material is preferably doped with a prescribed concentration of p-type material, so as to form a P-N junction with the underlying n-type base region. In FIG. 24, the hard mask layer 2102 is removed, followed by an optional CMP step to planarize the upper surface of the structure.

Figure 25:
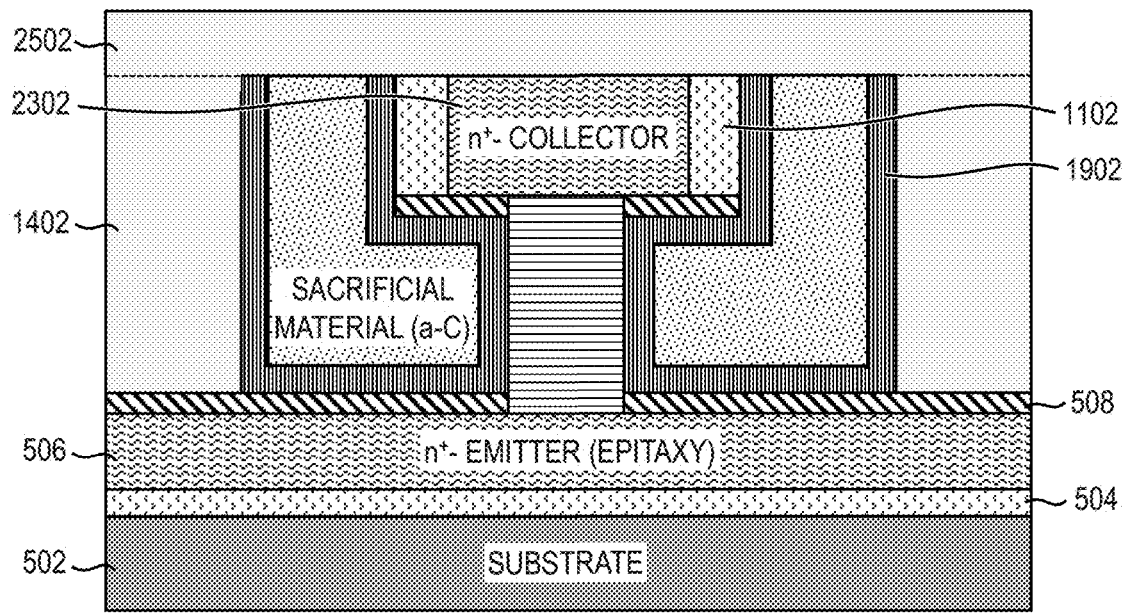

FIG. 25 depicts filling the structure with an ILD layer 2502 or a similar insulating material layer, so that ILD material is formed on the upper surface of the structure, on an upper surface of the existing insulating layer 1402, dielectric layer 1902, oxide layer 1102, and collector region 2302. The material used to form the ILD layer 2502 is preferably the same as the material used to form the insulating layer 1402, although in one or more alternative embodiments the materials used to form these layers can be different.

Figure 26:
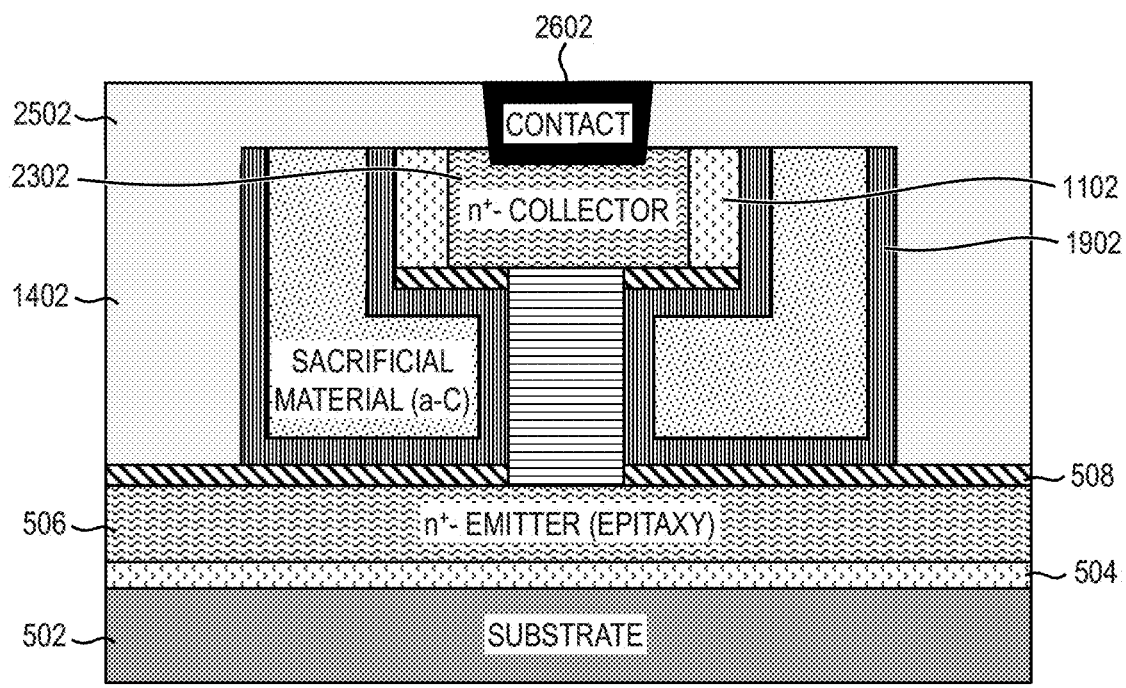

In FIG. 26, at least one opening in the ILD layer 2502 is formed, for example using known photolithographic patterning and etching, in which a collector contact 2602 is formed. The collector contact 2602 is preferably centered over the underlying collector region 2302 and has a smaller width relative to the collector region so that the contact does not make electrical connection with adjacent elements of the sensor structure. The collector contact 2602 provides electrical connection with the collector region 2302 of the BJT device. An emitter contact is also formed in this step, although not explicitly shown in FIG. 26 since it is out of the drawing plane (illustrative emitter contacts are depicted in the exemplary top plan view of FIG. 4A).

Figure 27:
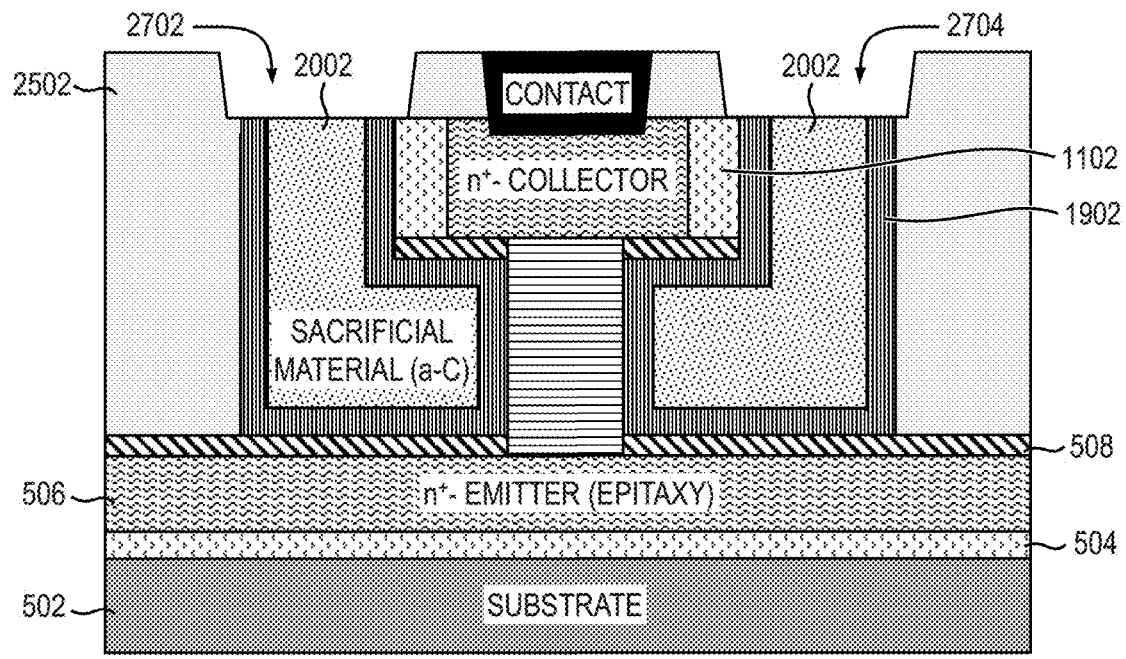
Figure 28:
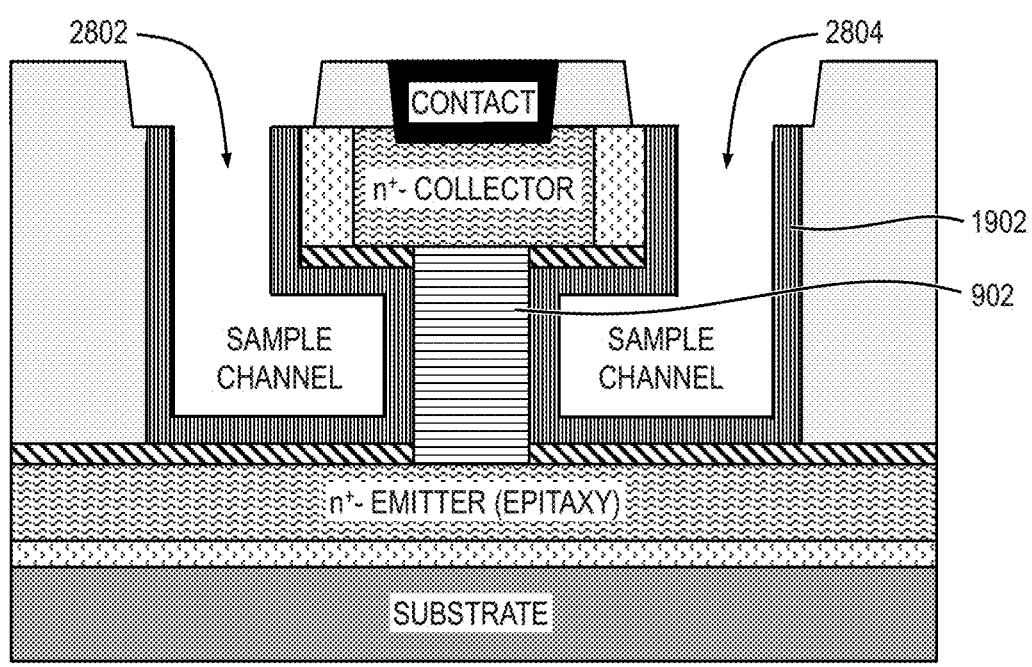

As depicted in FIG. 27, openings 2702 and 2704 are formed through the ILD layer 2502 (e.g., using standard patterning and etching) to thereby provide access to the channels of the sensing structure and remove the sacrificial material layer 2002 (e.g., a-C) filling the channels (e.g., channels 1504, 1506 shown in FIG. 19). The resulting structure with the sacrificial material layer 2002 removed to form sensing sample channels 2802 and 2804 is shown in FIG. 28. An important benefit achieved by one or more embodiments of the invention is that the sensing structure provides dual sensing channels that are embedded below an upper surface of the biosensor device, each sensing channel being disposed on opposing vertical sidewalls of the base region 902 of the integrated BJT device.

As previously stated, the oxide surface 1902 lining the channels 2802, 2804 is modified to provide a surface that specifically binds to select molecules. For example, to detect a specific protein (e.g., streptavidin), the surface of the channel oxide liner 1902 can be coated with a corresponding antibody (e.g., biotin) that specifically binds the proteins of interest. Since most bio-molecules are charged, bound bio-molecules would create charge on the surface of the channel oxide liner 1902 with a concomitant change in the base region 902 of the vertically oriented lateral BJT device, thus causing a shift in the turn-on voltage ($V_{BE}$) of the BJT device.

Figure 29:
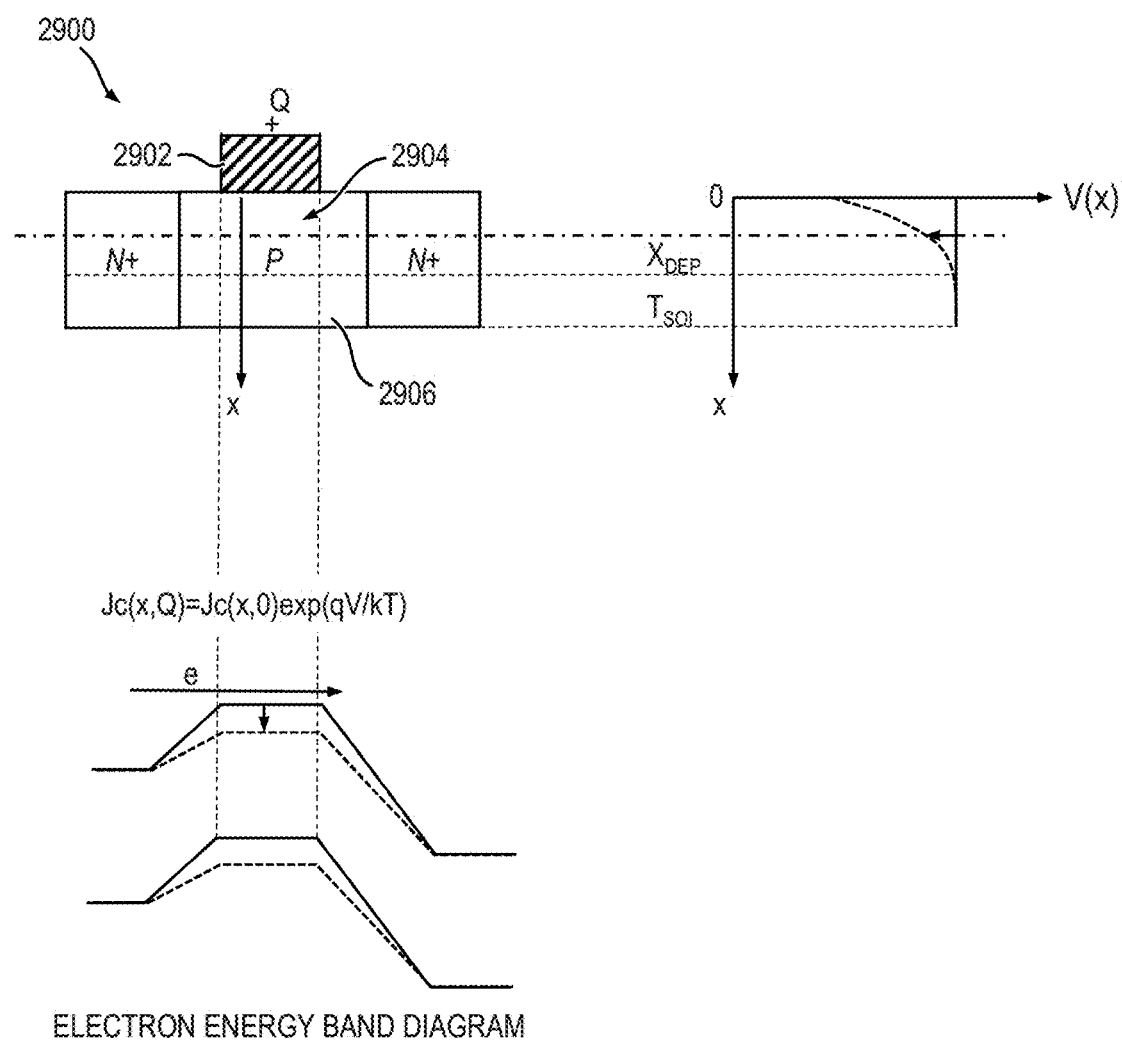
FIG. 29 conceptually depicts an exemplary approach for optimizing a sensitivity of the biosensor through careful design of the lateral SOI BJT structure in the biosensor, according to one or more embodiments of the present invention.

FIG. 29 conceptually depicts an exemplary approach for optimizing the sensitivity of a biosensor 2900 through careful design of the lateral SOI BJT structure in the biosensor, according to one or more embodiments of the invention. With reference to FIG. 29, positive charge, Q, bounded to the surface of an oxide sensing layer 2902 of the biosensor 2900 induces a depletion layer 2904 proximate the upper surface of an intrinsic base region 2906 of the lateral SOI BJT structure. A thickness (i.e., depth), $X_{DEP}$, of the depletion layer 2904 will be a function of an intrinsic base doping concentration, $N_B$, as evidenced by the following expression for charge Q:

$$Q = q N_B \cdot X_{DEP}, X_{DEP} < T_{SOI},$$

where q represents the magnitude of an electron charge and $T_{SOI}$ represents a thickness of the silicon layer of the SOI substrate; that is, the positive charge Q bounded on the surface of the oxide sensing layer 2902 induces an image charge of the same magnitude as Q in the depletion layer 2904.

Within the depletion layer 2904, the emitter-base (E-B) potential barrier is reduced, leading to an exponential increase in collector current ($I_{C1}$). Outside of the depletion layer 2904, collector current density is not affected ($I_{C2}$). To maximize the biosensor sensitivity, the depletion layer thickness should be comparable to SOI layer thickness ($X_{DEP} \sim T_{SOI}$). Sensitivity reduces when the base is fully depleted.

Consider the following derivation for computing collector current sensitivity, $I_C(Q)/I_C(0)$, where $I_C(Q)$ is the collector current when there is a positive charge Q bounded on the surface of oxide sensing layer 2902 and $I_C(0)$ is the collector current when there is no positive charge bounded on the surface of oxide sensing layer 2902:

$$V_S = \frac{q N_B}{2 \cdot \varepsilon_0 \varepsilon_{Si}} \cdot X_{DEP}^2$$

$$I_C(Q) = I_{C1} + I_{C2}$$

$$I_{C1} = I_C(0) \cdot \frac{X_{DEP}}{T_{SOI}} \cdot \frac{\int_0^{V_S} e^{qV/kT} dV}{\int_0^{V_S} dV}$$

$$= I_C(0) \cdot \frac{X_{DEP}}{T_{SOI}} \cdot \frac{kT}{qV_S} \cdot (e^{qV_S/kT} - 1)$$

$$I_{C2} = I_C(0) \cdot \frac{T_{SOI} - X_{DEP}}{T_{SOI}}$$

$$\frac{I_C(Q)}{I_C(0)} = \frac{X_{DEP}}{T_{SOI}} \cdot \frac{kT}{qV_S} \cdot (e^{qV_S/kT} - 1) + \frac{T_{SOI} - X_{DEP}}{T_{SOI}},$$

where $V_S$ is the maximum voltage lowering in the base region caused by the positive chare Q bounded on the surface of the oxide sensing layer 2902, $N_B$ is the dopant concentration in the base region, q is the magnitude of an electron charge, a is vacuum permittivity constant, $\varepsilon_{Si}$ is the dielectric constant of silicon, $X_{DEP}$ is the thickness of the depletion layer in the base region, $I_{C1}$ is a component of collector current flowing in the depleted portion of the base, $I_{C2}$ is a component of collector current flowing in the non-depleted portion of the base, $I_C(Q)$ is a sum of $I_{C1}$ and $I_{C2}$, and $T_{SOI}$ is the thickness of the SOI layer. As previously stated, when the depletion layer thickness is made comparable to SOI layer thickness (i.e., $X_{DEP} \sim T_{SOI}$), the expression for sensitivity $I_C(Q)/I_C(0)$ reduces to the following expression:

$$\frac{I_C(Q)}{I_C(0)} = \frac{kT}{qV_S} \cdot (e^{qV_S/kT} - 1).$$

Figures 30A, 30B:
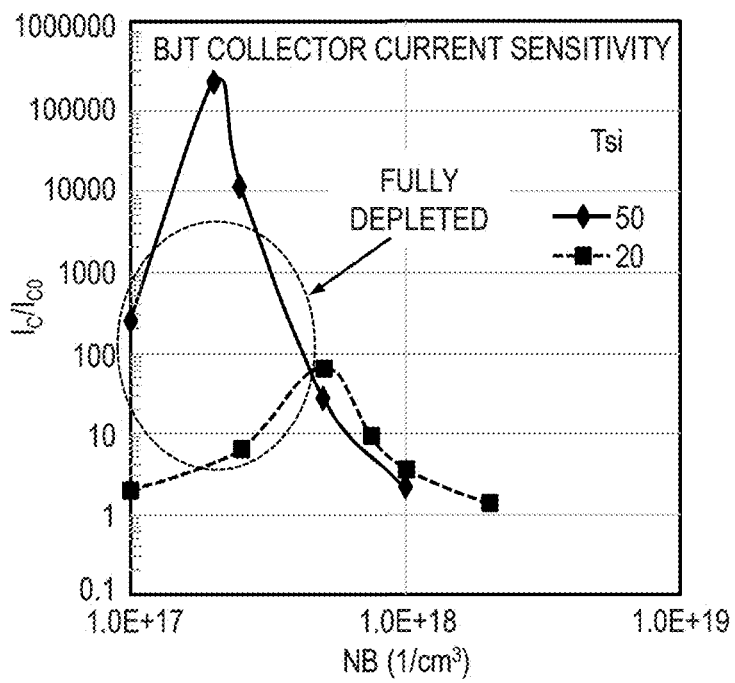
FIGS. 30A and 30B conceptually depict a comparison between illustrative BJT collector current sensitivities for two different thicknesses, namely, 20 nm and 50 nm, of the SOI layer, according to an exemplary embodiment of the present invention.

By way of example only and without limitation, FIGS. 30A and 30B are a graph and corresponding data table, respectively, depicting a comparison between illustrative lateral SOI BJT collector current sensitivities for two different depletion layer thicknesses, namely, $X_{DEP}$=20 nm and 50 nm, according to an embodiment of the invention. For this illustrative embodiment, single charge detection is assumed using a sensing window opening of about 10 nm×10 nm. For a small opening area of 10 nm×10 nm, a single charge corresponds to a charge density of 1e12/cm².

Simulation of sensing currents for this illustrative embodiment is made under the following conditions: emitter-base junction (diode) is forward biased at 0.6 V and collector current is monitored. The presence of the base contact enables the emitter-base junction to be forward-biased without requiring a reference electrode. The charges bound to the oxide sensing layer on top of the intrinsic base region are capacitively coupled to the base and modulate the sensing collector current $I_C$.

As shown in FIG. 30A, peak sensitivity for a given SOI thickness is achieved when the charge induces a fully depleted base from the top ($X_{DEP}=T_{SOI}$). In one or more embodiments, thicker SOI substrates can be designed with lighter doping concentration, $N_B$, for higher sensitivity. For example, with $T_{SOI}=50$ nm and $N_B=2e17/cm^3$, a peak sensitivity with collector current increase over 20,000 times can be expected.

The table illustrated in FIG. 30B depicts collector current sensitivities $I_C(Q)/I_C(0)$ for various exemplary parameters associated with the lateral SOI BJT of a biosensor according to an illustrative embodiment of the invention, where $J_{C1}(0)$ refers to the collector current with the given base and emitter/collector concentrations, and $J_{C1}$ refers to the change in collector current due to the barrier reduction in the base region caused by external charges from the bio-materials.

At least a portion of the techniques of the present invention may be implemented in an integrated circuit. In forming integrated circuits, identical die are typically fabricated in a repeated pattern on a surface of a semiconductor wafer. Each die includes a device described herein, and may include other structures and/or circuits. The individual die are cut or diced from the wafer, then packaged as an integrated circuit. One skilled in the art would know how to dice wafers and package die to produce integrated circuits. Any of the exemplary circuits illustrated in the accompanying figures, or portions thereof, may be part of an integrated circuit. Integrated circuits so manufactured are considered part of this invention.

Those skilled in the art will appreciate that the exemplary structures discussed above can be distributed in raw form (i.e., a single wafer having multiple unpackaged chips), as bare dies, in packaged form, or incorporated as parts of intermediate products or end products that benefit from having sensor devices therein formed in accordance with one or more embodiments of the invention.

An integrated circuit in accordance with aspects of the present disclosure can be employed in essentially any application and/or electronic system involving sensors that can detect and provide relevant environmental information, such as, but not limited to, biological molecules, radiation, chemical materials, inorganic particles, etc. Suitable systems for implementing embodiments of the invention may include, but are not limited to, biosensors. Systems incorporating such integrated circuits are considered part of this invention. Given the teachings of the present disclosure provided herein, one of ordinary skill in the art will be able to contemplate other implementations and applications of embodiments of the invention.

The illustrations of embodiments of the invention described herein are intended to provide a general understanding of the various embodiments, and they are not intended to serve as a complete description of all the elements and features of apparatus and systems that might make use of the circuits and techniques described herein. Many other embodiments will become apparent to those skilled in the art given the teachings herein; other embodiments are utilized and derived therefrom, such that structural and logical substitutions and changes can be made without departing from the scope of this disclosure. The drawings are also merely representational and are not drawn to scale. Accordingly, the specification and drawings are to be regarded in an illustrative rather than a restrictive sense.

Embodiments of the invention are referred to herein, individually and/or collectively, by the term "embodiment" merely for convenience and without intending to limit the scope of this application to any single embodiment or inventive concept if more than one is, in fact, shown. Thus, although specific embodiments have been illustrated and described herein, it should be understood that an arrangement achieving the same purpose can be substituted for the specific embodiment(s) shown; that is, this disclosure is intended to cover any and all adaptations or variations of various embodiments. Combinations of the above embodiments, and other embodiments not specifically described herein, will become apparent to those of skill in the art given the teachings herein.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. Terms such as "above" and "below" are used to indicate relative positioning of elements or structures to each other as opposed to relative elevation.

The corresponding structures, materials, acts, and equivalents of all means or step-plus-function elements in the claims below are intended to include any structure, material, or act for performing the function in combination with other claimed elements as specifically claimed. The description of the various embodiments has been presented for purposes of illustration and description, but is not intended to be exhaustive or limited to the forms disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the various embodiments with various modifications as are suited to the particular use contemplated.

The abstract is provided to comply with 37 C.F.R. § 1.72(b), which requires an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the appended claims reflect, inventive subject matter lies in less than all features of a single embodiment. Thus the following claims are hereby incorporated into the Detailed Description, with each claim standing on its own as separately claimed subject matter.

Given the teachings of embodiments of the invention provided herein, one of ordinary skill in the art will be able to contemplate other implementations and applications of the techniques of embodiments of the invention. Although illustrative embodiments of the invention have been described herein with reference to the accompanying drawings, it is to be understood that embodiments of the invention are not limited to those precise embodiments, and that various other changes and modifications are made therein by one skilled in the art without departing from the scope of the appended claims.

What is claimed is:

1. A biosensor, comprising:
    a bulk silicon substrate;
    a first vertically oriented lateral bipolar junction transistor (BJT) formed on at least a portion of the substrate, the first BJT including a first emitter region, a first collector region and a first epitaxially grown intrinsic base region between the first emitter and first collector regions; and
    a sensing structure formed on at least a portion of two vertical surfaces of the first intrinsic base region of the first BJT, the sensing structure including first and second channel/trench openings exposing the first intrinsic base region on first and second opposing sides thereof, respectively, and at least one dielectric layer formed in the first and second channel/trench openings and contacting at least a portion of the first intrinsic base region, the dielectric layer being configured to respond to charges in biological molecules.

2. The biosensor of claim 1, wherein the sensing structure further comprises a barrier layer formed on a surface of at least a portion of the dielectric layer, the barrier layer being configured to reduce a drift effect caused by ions from a biological molecule being tested penetrating into the dielectric layer of the sensing structure.

3. The biosensor of claim 2, wherein the barrier layer comprises a composite structure including a plurality of material layers, at least one of the material layers comprising a metal.

4. The biosensor of claim 3, wherein at least one of the material layers of the composite structure comprises gold.

5. The biosensor of claim 2, wherein a profile of at least one of the first and second channel/trench openings is centered around the first intrinsic base region.

6. The biosensor of claim 1, wherein the first BJT comprises at least a first emitter terminal in electrical contact with the first emitter region, at least a first collector terminal in electrical contact with the first collector region, and at least a first base terminal in electrical contact with the first intrinsic base region.

7. The biosensor of claim 6, wherein the first base terminal is positioned perpendicular to at least one of the first emitter terminal and first collector terminal.

8. The biosensor of claim 1, wherein the first and second channel/trench openings are isolated from one another, such that the biosensor is configured to concurrently sense two different biological materials introduced into the first and second channel/trench openings.

9. The biosensor of claim 1, further comprising a second vertically oriented lateral BJT formed on at least a portion of the substrate, the second BJT including a second emitter region, a second collector region and a second epitaxially grown intrinsic base region between the second emitter and second collector regions, wherein the sensing structure is formed on at least a portion of two vertical surfaces of the second intrinsic base region of the second BJT, the first intrinsic base region of the first BJT being accessible through the first channel/trench opening and the second intrinsic base region of the second vertical BJT being accessible through the second channel/trench opening.

10. The biosensor of claim 9, further comprising a first emitter terminal in electrical contact with the first emitter region of the first BJT, a second emitter terminal in electrical contact with the second emitter region of the second BJT, a first collector terminal in electrical contact with the first collector region of the first BJT, a second collector terminal in electrical contact with the second collector region of the second BJT, a first base terminal in electrical contact with the first intrinsic base region of the first BJT, and a second base terminal in electrical contact with the second intrinsic base region of the second BJT.

11. The biosensor of claim 10, wherein the first and second channel/trench openings are isolated from one another, such that the biosensor is configured to concurrently sense two different biological materials introduced into the first and second channel/trench openings.

12. The biosensor of claim 9, further comprising an emitter terminal in electrical contact with the first and second emitter regions, a first collector terminal in electrical contact with the first collector region, a second collector terminal in electrical contact with the second collector region, and a base terminal in electrical contact with the first and second intrinsic base regions, wherein the sensing structure is formed on at least a portion of two vertical surfaces of the first and second intrinsic base regions, the sensing structure including first and second channel/trench openings for accessing the first and second intrinsic base regions, respectively, wherein the first BJT is a vertically oriented lateral NPN BJT and the second BJT is a vertically oriented lateral PNP BJT, the biosensor being configured to provide self-calibrated charge sensing.

13. The biosensor of claim 9, wherein the first and second channel/trench openings are adapted to convey a fluid to be tested below a planar upper surface of the biosensor and proximate to opposing vertical sidewalls of the first and second intrinsic base regions of the first BJT and second BJT, respectively.

14. The biosensor of claim 1, wherein the first and second channel/trench openings are configured so as not to extend above a planar upper surface of the biosensor.

15. The biosensor of claim 14, wherein the first and second channel/trench openings are configured to convey a fluid to be tested below the planar upper surface of the biosensor and proximate to opposing vertical sidewalls of the first intrinsic base region of the first BJT.

* * * * *